(12) United States Patent
Leveillard et al.

(10) Patent No.: US 11,865,189 B2
(45) Date of Patent: Jan. 9, 2024

(54) TRANSGENIC RPE CELLS OVEREXPRESSING OTX2 FOR THE TREATMENT OF RETINAL DEGENERATION

(71) Applicants: SORBONNE UNIVERSITE, Paris (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

(72) Inventors: Thierry Leveillard, Maison-Alfort (FR); Christo Kole, Chatenay Malabry (FR); Jose-Alain Sahel, Paris (FR)

(73) Assignees: SORBONNE UNIVERSITE, Paris (FR); CENTRE NATIONAL DE LA RECHERCHE SCIENTIFIQUE, Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 15/536,725

(22) PCT Filed: Dec. 17, 2015

(86) PCT No.: PCT/EP2015/080288
§ 371 (c)(1),
(2) Date: Jun. 16, 2017

(87) PCT Pub. No.: WO2016/097183
PCT Pub. Date: Jun. 23, 2016

(65) Prior Publication Data
US 2017/0348434 A1    Dec. 7, 2017

(30) Foreign Application Priority Data
Dec. 18, 2014    (EP) .................................... 14307069

(51) Int. Cl.
| | | |
|---|---|---|
| *A61K 48/00* | (2006.01) | |
| *C12N 5/079* | (2010.01) | |
| *C12N 15/864* | (2006.01) | |
| *A61K 35/12* | (2015.01) | |
| *C12N 7/00* | (2006.01) | |
| *C12N 5/16* | (2006.01) | |

(52) U.S. Cl.
CPC .......... *A61K 48/0058* (2013.01); *A61K 35/12* (2013.01); *A61K 48/00* (2013.01); *C12N 5/0621* (2013.01); *C12N 5/16* (2013.01); *C12N 7/00* (2013.01); *C12N 15/8645* (2013.01); *C12N 2510/00* (2013.01); *C12N 2750/14141* (2013.01)

(58) Field of Classification Search
CPC .... A61K 48/0058; A61K 35/12; A61K 48/00; A61K 35/30; C12N 5/0621; C12N 5/16; C12N 7/00; C12N 15/8645; C12N 2510/00; C12N 2750/14141; A61P 9/10; A61P 27/02
See application file for complete search history.

(56) References Cited

U.S. PATENT DOCUMENTS

2013/0149284 A1* 6/2013 Malcuit .................. A61P 27/02
424/93.7

FOREIGN PATENT DOCUMENTS

| EP | 1 591 127 | 11/2005 |
| JP | 2010-524457 | 7/2010 |
| JP | 2011-500024 | 1/2011 |
| KR | 2015 0042598 | 4/2015 |
| WO | WO 2008/129554 | 10/2008 |
| WO | WO 2009/051671 | 4/2009 |
| WO | WO 2009/132156 | 10/2009 |
| WO | WO 2011/063005 | 5/2011 |
| WO | WO 2013/074681 | 5/2013 |

OTHER PUBLICATIONS

Singh et al (Invest Ophthalmol Vis Sci, 54: 6767-6778m 2013) (Year: 2013).*
Wang et al (Expert Opin Biol Ther, 10(8): 1227-1239, 2010) (Year: 2010).*
Yvon et al (Computational and Structural Biotechnology Journal 13 (2015) 382-389) (Year: 2015).*
Leach et al (Tem Cells, 33:2363-2373, 2015) (Year: 2015).*
Lund et al, (J. Leukoc. Biol. 74: 151-160; 2003) (Year: 2003).*
Da Cruz et al, (Progress in Retinal and Eye Research 26 (2007) 598-635) (Year: 2007).*
Abe et al (PLoS One, 5(7): e11673-e11673, 2010) (Year: 2010).*
Beby et al (PLoS One, 5(7): e11673-e11673, 2010) (Year: 2010).*
Glubrecht et al (J. Neurochem. (2009) 111, 250-263) (Year: 2009).*
Yan et al, (Science 290: 523-527, 2000) (Year: 2000).*
Holland et al, (Phil. Trans. R. Soc. B, 372:1-11, 2016) (Year: 2016).*
Skolnick et al. (2000, Trends in Biotech. 18:34-39) (Year: 2000).*
Nazari, (Progress in Retinal and Eye Research 48 (2015) 1e39, 2-30 2015, (Year: 2015).*
Gupta, J Neural Eng, 14: 1-20, 2017 (Year: 2017).*
Slijkerman, Progress in Retinal Research, 48: 137-139, 2915) (Year: 2015).*
Methods and Protocols, edited by Snyder and Moullier, p. 1-469, 2011 (Year: 2011).*

(Continued)

*Primary Examiner* — Valarie E Bertoglio
*Assistant Examiner* — Constantina E Stavrou
(74) *Attorney, Agent, or Firm* — SALIWANCHIK, LLOYD & EISENSCHENK

(57) ABSTRACT

The present invention relates to methods and composition for use in the treatment of retinal degeneration, in particular retinal degeneration due to retinal pigment epithelium dysfunction.

18 Claims, 12 Drawing Sheets
Specification includes a Sequence Listing.

(56) References Cited

OTHER PUBLICATIONS

Trapani et al, Prog Retin Eye Res, 2014, 108-128. (Year: 2014).*
Capra et al, Viral-vector therapies at scale: Today's challenges and future opportunities, McKinsey & Company, 2022; (Year: 2022).*
Ellis et al, Virology Journal, 2013, 10:74 (Year: 2013).*
Bertolotti, E. et al. "Stem cells as source for retinal pigment epithelium transplantation" *Progress in Retinal and Eye Research*, Jun. 13, 2014, pp. 130-144, vol. 42.
Chiba, C. et al. "Intraocular implantation of DNA-transfected retinal pigment epithelium cells: a new approach for analyzing molecular functions in the newt retinal regeneration" *Neuroscience Letters*, Sep. 23, 2004, pp. 171-175, vol. 368, No. 2.
Housset, M. et al. "Loss of Otx2 in the Audit Retina Disrupts Retinal Pigment Epithelium Function, Causing Photoreceptor Degeneration" *The Journal of Neuroscience*, Jun. 12, 2013, pp. 9890-9904, vol. 33, No. 24.
Martinez-Morales, J. R. et al. "OTX2 Activates the Molecular Network Underlying Retina Pigment Epithelium Differentiation" *The Journal of Biological Chemistry*, Jun. 13, 2003, pp. 21721-21731, vol. 278, No. 24.
Reinisalo, M. et al. "Regulation of the human tyrosinase gene in retinal pigment epithelium cells: the significance of transcription factor orthodenticle homeobox 2 and its polymorphic binding site" *Molecular Vision*, Jan. 10, 2012, pp. 38-54, vol. 18.
Roger, J. E. et al. "OTX2 loss causes rod differentiation defect in CRX-associated congenital blindness" *The Journal of Clinical Investigation*, Feb. 2014, pp. 631-643, vol. 124, No. 2.
Choi, S. W. et al. "miR-410 Inhibition Induces RPE Differentiation of Amniotic Epithelial Stem Cells via Overexpression of OTX2 and RPE65" *Stem Cell Reviews and Reports*, Oct. 29, 2014, pp. 1-11.
Written Opinion in International Application No. PCT/EP2015/080288, dated Feb. 9, 2016, pp. 1-8.
Housset, M. et al. "Loss of Otx2 in the Adult Retina Disrupts Retinal Pigment Epithelium Function, Causing Photoreceptor Degeneration" *The Journal of Neuroscience*, Jun. 12, 2013, pp. 9890-9904, vol. 33, No. 24.
Sergouniotis, P. I. et al. "Recessive Mutations in KCNJ13, Encoding an Inwardly Rectifying Potassium Channel Subunit, Cause Leber Congenital Amaurosis" *The American Journal of Human Genetics*, Jul. 15, 2011, pp. 183-190, vol. 89.
Allikmets, R. et al. "A photoreceptor cell-specific ATP-binding transporter gene (ABCR) is mutated in recessive Stargardt macular dystrophy" *Nature Genetics*, Mar. 1997, pp. 236-246, vol. 15.
Ayyagari, R. et al. "X-Linked Recessive Atrophic Macular Degeneration from RPGR Mutation" *Genomics*, Aug. 2002, pp. 166-171, vol. 80, No. 2.
Wada, Y. et al. "Autosomal Dominant Macular Degeneration Associated with 208 delG Mutation in the FSCN2 Gene" *Arch Ophthalmol*, Nov. 2003, pp. 1613-1620, vol. 121.
Puche, N. et al. "High-resolution spectral-domain optical coherence tomography (SD OCT) features in adult onset foveomacular vitelliform dystrophy" *British Journal of Ophthalmology*, 2010, pp. 1-30, vol. 94, No. 9.
Abràmoff, M. D. et al. "Human Photoreceptor Outer Segments Shorten During Light Adaptation" *IOVS*, May 2013, pp. 3721-3728, vol. 54, No. 5.
Ray, K. et al. "Tyrosinase and ocular diseases: Some novel thoughts on the molecular basis of oculocutaneous albinism type 1" *Progress in Retinal and Eye Research*, 2007, pp. 323-358, vol. 26.
Fritsche, L. G. et al. "Seven New Loci Associated with Age-Related Macular Degeneration" *Nature Genetics*, Apr. 2013, pp. 1-28, vol. 45, No. 4.
Freund, C. L et al. "De novo mutations in the CRX homeobox gene associated with Leber congenital amaurosis" *Nature Genetics*, Apr. 1998, pp. 311-312, vol. 18.
Sohocki, M. M. et al. "A Range of Clinical Phenotypes Associated with Mutations in CRX, a Photoreceptor Transcription-Factor Gene" *Am. J. Hum. Genet.*, 1998, pp. 1307-1315, vol. 63.
Vuori, N. et al. "CACNB2 Is a Novel Susceptibility Gene for Diabetic Retinopathy in Type 1 Diabetes" *Diabetes*, Nov. 2019, pp. 2165-2174, vol. 68.
Freund, C. L et al. "Cone-Rod Dystrophy Due to Mutations in a Novel Photoreceptor-Specific Homeobox Gene (CRX) Essential for Maintenance of the Photoreceptor" *Cell*, Nov. 14, 1997, pp. 543-553, vol. 91.

* cited by examiner

| Gene symbol | Gene name | NCBI accession N° | Relative expression ($2^{-\Delta\Delta Ct}$) | P value |
|---|---|---|---|---|
| Down-regulated genes | | | | |
| BEST1 | Bestrophin 1 | XM_003353833.1 | 0.043 | < 0.0001 |
| BMP4 | Bone morphogenetic protein 4 | NM_001101031.2 | 0.132 | < 0.0001 |
| CACNB2 | Calcium channel voltage dependent beta 2 | XM_003482816.1 | 0.161 | < 0.0001 |
| CLDN19 | Claudin-19 | NM_001160084.1 | 0.580 | 0.0006 |
| CRX | Cone-road homebox | XM_003127265.1 | 0.001 | < 0.0001 |
| CTSD | Cathepsin D | NM_001037721.1 | 0.108 | < 0.0001 |
| DCT | Dopachrome tautomerase | NM_001025227.1 | 0.001 | < 0.0001 |
| FADS1 | Fatty acid desaturase 1 | NM_001113041.1 | 0.526 | 0.0002 |
| ITGB5 | Integrin, beta 5 | NM_001246669.1 | 0.427 | < 0.0001 |
| KCNJ13 | Potassium inwardly rectifying channel subfamily J,13 | XM_001926506.3 | 0.033 | < 0.0001 |
| KRT8 | Keratin 8 | NM_001159615.1 | 0.364 | < 0.0001 |
| KRT18 | Keratin 18 | XM_003126180.3 | 0.058 | < 0.0001 |
| LHX2 | Lim homeobox protein 2 | NM_001170519.1 | 0.452 | 0.0004 |
| LRAT | Lecithin-retinol acyltransferase | NM_001244920.1 | 0.014 | < 0.0001 |
| LRP8 | Apolipoprotein e receptor | NM_001199891.1 | 0.365 | < 0.0001 |
| MERTK | C-mer proto-oncogene tyrosine kinase | XM_003124812.3 | 0.052 | < 0.0001 |
| MKI67 | Marker of proliferation ki-67 | NM_001101827.1 | 0.338 | < 0.0001 |
| OTX2 | Orthodenticle homolog 2 | XM_003353491.1 | 0.422 | < 0.0001 |
| PMEL | Premelanosome protein | XM_003481626.1 | 0.018 | < 0.0001 |
| RDH10 | Retinol dehydrogenase 10 | XM_001928082.3 | 0.031 | < 0.0001 |
| RPE65 | Retinal pigment epithelium 65 kDa | XM_003127931.2 | 0.088 | < 0.0001 |
| SERPINF1 | Serpin peptidase inhibitor | NM_001078662.1 | 0.207 | < 0.0001 |
| SLC16A8 | Solute carrier family 16, member 8 | XM_003126028.1 | 0.023 | < 0.0001 |
| SLC24A5 | Solute carrier family 24, member 5 | XM_003121523.1 | 0.261 | < 0.0001 |
| SLC39A12 | Solute carrier family 39, member 12 | XM_003130728.1 | 0.023 | < 0.0001 |
| TRPM3 | Transient receptor potential cation channel | XM_001925032.3 | 0.551 | 0.0008 |
| Up-regulated genes | | | | |
| SLC16A3 | Solute carrier family 16, member 3 | XM_003357925.1 | 13.193 | 0.0002 |
| SLC16A12 | Solute carrier family 16, member 12 | XM_001928811.2 | 2.885 | < 0.0001 |
| TYRP1 | Tyrosinase related protein 1 | NM_001025226.1 | 48.561 | < 0.0001 |

Figure 12

| Gene symbol | Gene name | Relative expression ($2^{-\Delta\Delta Ct}$) | | P value |
| --- | --- | --- | --- | --- |
| | | RPE-OTX2 | RPE-OTX2L | |
| CACNB2 | Calcium channel voltage dependent beta 2 | 1.59 | - | 0.002 |
| CLDN19 | Claudin-19 | 0.42 | 0.41 | 0.003 |
| CRX | Cone-road homebox | 18.88 | 18.12 | < 0.0001 |
| DCT | Dopachrome tautomerase | 8.68 | 4.77 | < 0.0001 |
| KCNJ13 | Potassium inwardly rectifying channel subfamily J,13 | 9 | 6.77 | < 0.0001 |
| KRT18 | Keratin 18 | 2.45 | 2.68 | < 0.0001 |
| MKI67 | Marker of proliferation ki-67 | 1.67 | - | 0.0005 |
| RDH10 | Retinol dehydrogenase 10 | 3.36 | 2.87 | < 0.0001 |
| RPE65 | Retinal pigment epithelium 65 kDa | - | 0.42 | 0.003 |
| SLC16A8 | Solute carrier family 16, member 8 | 2.52 | 2.79 | < 0.0001 |
| SLC16A12 | Solute carrier family 16, member 12 | 4.91 | 3.06 | < 0.0001 |
| SLC39A12 | Solute carrier family 39, member 12 | 0.44 | 0.42 | < 0.004 |
| TYR | Tyrosinase | 13.42 | 10.92 | 0.0008 |
| TYRP1 | Tyrosinase related protein 1 | 2.66 | 2.48 | < 0.0001 |

Figure 13

```
                        SEQUENCE LISTING

<160> NUMBER OF SEQ ID NOS: 18

<210> SEQ ID NO 1
<211> LENGTH: 37
<212> TYPE: DNA
<213> ORGANISM: Artificial Sequence
<220> FEATURE:
<223> OTHER INFORMATION: OTX2 forward primer

<400> SEQUENCE: 1
gtgtccaggc ggccgcaaaa atgatgtctt atctaaa                              37

<210> SEQ ID NO 2
<211> LENGTH: 38
<212> TYPE: DNA
<213> ORGANISM: Artificial Sequence
<220> FEATURE:
<223> OTHER INFORMATION: OTX2 reverse primer

<400> SEQUENCE: 2
aatcggatcc cgatatctca caaaacctgg aatttcca                             38

<210> SEQ ID NO 3
<211> LENGTH: 21
<212> TYPE: DNA
<213> ORGANISM: Artificial Sequence
<220> FEATURE:
<223> OTHER INFORMATION: ITR sequence forward primer

<400> SEQUENCE: 3 ggaacccta gtgatggagt t                                                21

<210> SEQ ID NO 4
<211> LENGTH: 16
<212> TYPE: DNA
<213> ORGANISM: Artificial Sequence
<220> FEATURE:
<223> OTHER INFORMATION: ITR sequence reverse primer

<400> SEQUENCE: 4
cggcctcagt gagcga                                                     16

<210> SEQ ID NO 5
<211> LENGTH: 20
<212> TYPE: DNA
<213> ORGANISM: Artificial Sequence
<220> FEATURE:
<223> OTHER INFORMATION: KCNJ13 forward primer

<400> SEQUENCE: 5
gcaggccttc catgatttta                                                 20
```

<210> SEQ ID NO 6
<211> LENGTH: 20
<212> TYPE: DNA
<213> ORGANISM: Artificial Sequence
<220> FEATURE:
<223> OTHER INFORMATION: KCNJ13 reverse primer

<400> SEQUENCE: 6
tgagctgtca gatggctttg        20

<210> SEQ ID NO 7
<211> LENGTH: 20
<212> TYPE: DNA
<213> ORGANISM: Artificial Sequence
<220> FEATURE:
<223> OTHER INFORMATION: SLC16A12 forward primer

<400> SEQUENCE: 7
tgcctgtccc actaggaagt        20

<210> SEQ ID NO 8
<211> LENGTH: 20
<212> TYPE: DNA
<213> ORGANISM: Artificial Sequence
<220> FEATURE:
<223> OTHER INFORMATION: SLC16A12 reverse primer

<400> SEQUENCE: 8
gcatcatttg ccatgtgact        20

<210> SEQ ID NO 9
<211> LENGTH: 20
<212> TYPE: DNA
<213> ORGANISM: Artificial Sequence
<220> FEATURE:
<223> OTHER INFORMATION: RDH10 forward primer

<400> SEQUENCE: 9
ggcaacaagt cccacctaaa        20

<210> SEQ ID NO 10
<211> LENGTH: 20
<212> TYPE: DNA
<213> ORGANISM: Artificial Sequence
<220> FEATURE:
<223> OTHER INFORMATION: RDH10 reverse primer

<400> SEQUENCE: 10
gtttacttgg tgggggaggt        20

<210> SEQ ID NO 11
<211> LENGTH: 20
<212> TYPE: DNA
<213> ORGANISM: Artificial Sequence
<220> FEATURE:
<223> OTHER INFORMATION: TYRP1 forward primer

<400> SEQUENCE: 11
ccaatttgca gggaacaaat        20

<210> SEQ ID NO 12
<211> LENGTH: 21
<212> TYPE: DNA
<213> ORGANISM: Artificial Sequence
<220> FEATURE:

-continued

<223> OTHER INFORMATION: TYRP1 reverse primer

<400> SEQUENCE: 12
tgccttaaat tgccttctca a                                           21

<210> SEQ ID NO 13
<211> LENGTH: 20
<212> TYPE: DNA
<213> ORGANISM: Artificial Sequence
<220> FEATURE:
<223> OTHER INFORMATION: HGB forward primer

<400> SEQUENCE: 13
gaacgtcagg attcccttga                                             20

<210> SEQ ID NO 14
<211> LENGTH: 20
<212> TYPE: DNA
<213> ORGANISM: Artificial Sequence
<220> FEATURE:
<223> OTHER INFORMATION: HGB reverse primer

<400> SEQUENCE: 14
ccattgggag cttccttgta                                             20

<210> SEQ ID NO 15
<211> LENGTH: 289
<212> TYPE: PRT
<213> ORGANISM: Homo sapiens

<400> SEQUENCE: 15

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
            20                  25                  30

Ala Thr Pro Arg Lys Gln Arg Arg Glu Arg Thr Thr Phe Thr Arg Ala
        35                  40                  45

Gln Leu Asp Val Leu Glu Ala Leu Phe Ala Lys Thr Arg Tyr Pro Asp
    50                  55                  60

Ile Phe Met Arg Glu Glu Val Ala Leu Lys Ile Asn Leu Pro Glu Ser
65                  70                  75                  80

Arg Val Gln Val Trp Phe Lys Asn Arg Arg Ala Lys Cys Arg Gln Gln
                85                  90                  95

Gln Gln Gln Gln Gln Asn Gly Gly Gln Asn Lys Val Arg Pro Ala Lys
            100                 105                 110

Lys Lys Thr Ser Pro Ala Arg Glu Val Ser Ser Glu Ser Gly Thr Ser
        115                 120                 125

Gly Gln Phe Thr Pro Pro Ser Ser Thr Ser Val Pro Thr Ile Ala Ser
    130                 135                 140

Ser Ser Ala Pro Val Ser Ile Trp Ser Pro Ala Ser Ile Ser Pro Leu
145                 150                 155                 160

Ser Asp Pro Leu Ser Thr Ser Ser Cys Met Gln Arg Ser Tyr Pro
                165                 170                 175

Met Thr Tyr Thr Gln Ala Ser Gly Tyr Ser Gln Gly Tyr Ala Gly Ser
            180                 185                 190

Thr Ser Tyr Phe Gly Gly Met Asp Cys Gly Ser Tyr Leu Thr Pro Met
        195                 200                 205

His His Gln Leu Pro Gly Pro Gly Ala Thr Leu Ser Pro Met Gly Thr
    210                 215                 220

Asn Ala Val Thr Ser His Leu Asn Gln Ser Pro Ala Ser Leu Ser Thr
225                 230                 235                 240

Gln Gly Tyr Gly Ala Ser Ser Leu Gly Phe Asn Ser Thr Thr Asp Cys
            245                 250                 255

Leu Asp Tyr Lys Asp Gln Thr Ala Ser Trp Lys Leu Asn Phe Asn Ala
        260                 265                 270

Asp Cys Leu Asp Tyr Lys Asp Gln Thr Ser Ser Trp Lys Phe Gln Val
        275                 280                 285

Leu

<210> SEQ ID NO 16
<211> LENGTH: 297
<212> TYPE: PRT
<213> ORGANISM: Homo sapiens

<400> SEQUENCE: 16

Met Met Ser Tyr Leu Lys Gln Pro Pro Tyr Ala Val Asn Gly Leu Ser
1               5                   10                  15

Leu Thr Thr Ser Gly Met Asp Leu Leu His Pro Ser Val Gly Tyr Pro
                20                  25                  30

Gly Pro Trp Ala Ser Cys Pro Ala Ala Thr Pro Arg Lys Gln Arg Arg
            35                  40                  45

Glu Arg Thr Thr Phe Thr Arg Ala Gln Leu Asp Val Leu Glu Ala Leu
    50                  55                  60

Phe Ala Lys Thr Arg Tyr Pro Asp Ile Phe Met Arg Glu Glu Val Ala
65                  70                  75                  80

Leu Lys Ile Asn Leu Pro Glu Ser Arg Val Gln Val Trp Phe Lys Asn
                85                  90                  95

Arg Arg Ala Lys Cys Arg Gln Gln Gln Gln Gln Gln Asn Gly Gly
            100                 105                 110

Gln Asn Lys Val Arg Pro Ala Lys Lys Lys Thr Ser Pro Ala Arg Glu
        115                 120                 125

Val Ser Ser Glu Ser Gly Thr Ser Gly Gln Phe Thr Pro Pro Ser Ser
    130                 135                 140

Thr Ser Val Pro Thr Ile Ala Ser Ser Ser Ala Pro Val Ser Ile Trp
145                 150                 155                 160

Ser Pro Ala Ser Ile Ser Pro Leu Ser Asp Pro Leu Ser Thr Ser Ser
                165                 170                 175

Ser Cys Met Gln Arg Ser Tyr Pro Met Thr Tyr Thr Gln Ala Ser Gly
            180                 185                 190

Tyr Ser Gln Gly Tyr Ala Gly Ser Thr Ser Tyr Phe Gly Gly Met Asp
        195                 200                 205

Cys Gly Ser Tyr Leu Thr Pro Met His His Gln Leu Pro Gly Pro Gly
    210                 215                 220

Ala Thr Leu Ser Pro Met Gly Thr Asn Ala Val Thr Ser His Leu Asn
225                 230                 235                 240

Gln Ser Pro Ala Ser Leu Ser Thr Gln Gly Tyr Gly Ala Ser Ser Leu
                245                 250                 255

Gly Phe Asn Ser Thr Thr Asp Cys Leu Asp Tyr Lys Asp Gln Thr Ala
            260                 265                 270

Ser Trp Lys Leu Asn Phe Asn Ala Asp Cys Leu Asp Tyr Lys Asp Gln
        275                 280                 285

Thr Ser Ser Trp Lys Phe Gln Val Leu
        290                 295

```
<210> SEQ ID NO 17
<211> LENGTH: 27
<212> TYPE: DNA
<213> ORGANISM: Artificial Sequence
<220> FEATURE:
<223> OTHER INFORMATION: OTX2 forward primer

<400> SEQUENCE: 17
cttcctactt tgggggcatg gactgtg                                              27

<210> SEQ ID NO 18
<211> LENGTH: 27
<212> TYPE: DNA
<213> ORGANISM: Artificial Sequence
<220> FEATURE:
<223> OTHER INFORMATION: OTX2 reverse primer

<400> SEQUENCE: 18
gcattggtac ccatgggact gagtgtg                                              27
```

TRANSGENIC RPE CELLS OVEREXPRESSING OTX2 FOR THE TREATMENT OF RETINAL DEGENERATION

CROSS-REFERENCE TO RELATED APPLICATION

This application is the U.S. national stage application of International Patent Application No. PCT/EP2015/080288, filed Dec. 17, 2015.

The Sequence Listing for this application is labeled "Seq-List.txt" which was created on Jun. 8, 2017 and is 9 KB. The entire content of the sequence listing is incorporated herein by reference in its entirety.

FIELD OF THE INVENTION

The present invention relates to the field of medicine, in particular to the treatment of retinal degeneration.

BACKGROUND OF THE INVENTION

Retinitis pigmentosa is an inhered retinal degeneration characterized clinically by two successive phases. Nyctalopia or nigh blindness, which constitutes the first symptom corresponds to a moderate handicap for the patients as compared to the second phase of reduction of the visual field that is often leading to total blindness. These two phases result from two waves of photoreceptor degeneration, the rods which are responsible of vision at low luminance, and the cones from which relies vision during daytime.

Retinitis pigmentosa is the most prevalent form of inherited retinal degenerations. These diseases are characterized genetically by their extreme heterogeneity. While a severe form of recessive inherited retinal degeneration, Leber congenital amaurosis can be successfully treated by corrective gene therapy when the disease results from mutation in the RPE65 gene, the global impact on the disease is limited to those patients (Bennett et al., 2012).

The cost of that personalized therapy has led to the development of approaches that are independent of the causative genes. Trophic factors as ciliary neurotrophic factor (CNTF) have been used successfully to prevent photoreceptor degeneration in several models of retinitis pigmentosa, such as the rd1 mouse (LaVail et al., 1998). Nevertheless, a clinical trial using CNTF delivered by encapsulated cell intraocular implants has failed to demonstrate visual benefice for patients with retinitis pigmentosa (Birch et al., 2013).

The replacement of photoreceptor loss by transplantation has been envisioned, but the problem of the reconnection of the grafted photoreceptors with the bipolar cells in the inner retina remained for a long time a barrier for the clinical development of such strategy (Litchfield et al., 1997). This problem has been solved for the rd1 mouse by transplanting photoreceptor precursors at a very specific stage of their differentiation (MacLaren et al., 2006). Unfortunately, this period of photoreceptor differentiation in human limits considerably its transfer to the clinic (Léveillard et al., 2007).

In the meantime, because of the essential role of cones for vision, the efforts have been concentrated on the prevention of secondary cone loss in retinitis pigmentosa. The identification of rod-derived cone viability factor (RdCVF) initiates a therapeutic development based on the administration of this novel trophic factor to prevent cone degeneration and vision loss in patients suffering from retinitis pigmentosa (Léveillard et al. 2004, Byrne et al. 2015). The strategy relies on the physiological interaction between the rods and the cones. The gene encoding RdCVF, the nucleoredoxin like 1 (NXNL1), is expressed in a rod dependent manner and is consequently switched off following rod loss during the first phase of the disease (Reichman et al. 2010). Since a significant proportion of genes causing retinitis pigmentosa are expressed specifically by rods and not by cones, like the rhodopsin gene RHO, RdCVF is presumably a treatment that would be applied almost independently of the causative gene (Byrne et al. 2015, Yang et al. 2009).

However, it is rather unlikely that RdCVF would be efficient in treating retinitis pigmentosa resulting from a gene defect in retinal pigmented epithelium (RPE). As shown early on, in this configuration, transplantation of healthy RPE cells is a better strategy (Gouras et al. 1989). Such approach, while rational, has only led up today to limited success considering visual function as compared strictly to photoreceptor survival observed in animal models (Da Cruz et al. 2007).

Accordingly, there is a significant need for an improved strategy to treat retinal diseases resulting from degeneration or dysfunction of retinal pigmented epithelium.

SUMMARY OF THE INVENTION

The inventors herein demonstrated that an increased intracellular level of OTX2 protein in RPE cells improves the benefice of transplantation of these cells on photoreceptor survival.

Accordingly, in a first aspect, the present invention relates to retinal pigment epithelial (RPE) cells engineered to increase the intracellular level of OTX2 protein for use in the treatment of retinal degeneration.

OTX2 protein may be a native mammalian OTX2 protein, or a variant or functional fragment thereof. In particular, this protein may comprise, or consist of, the amino acid sequence set forth in SEQ ID NO: 15, or SEQ ID NO: 16, or any variant or fragment thereof. Preferably, OTX2 protein comprises, or consists of, the amino acid sequence set forth in SEQ ID NO: 15, or SEQ ID NO: 16.

RPE cells to be modified may be obtained from differentiation of stem cells, preferably from differentiation of induced pluripotent stem (iPS) cells, into RPE cells.

In a preferred embodiment, RPE cells are genetically engineered to over-express OTX2 protein. These cells may be genetically engineered by introducing a recombinant nucleic acid sequence encoding OTX2 protein operably linked to one or more control sequences. In particular, they may be genetically engineered by introducing a recombinant viral vector, preferably an adenovirus, adeno-associated virus or lentivirus vector, comprising a nucleic acid sequence encoding OTX2 protein operably linked to one or more control sequences.

Preferably, the level of OTX2 protein in engineered RPE cells is, after normalization, at least 1.5-fold higher, than the level of OTX2 protein in non-engineered RPE cells.

Preferably, RPE cells are administered to the subject in need thereof by intraocular injection, preferably by injection into the subretinal space of the eye.

In another aspect, the present invention further relates to a pharmaceutical composition comprising RPE cells engineered to increase the level of OTX2 protein, preferably genetically engineered to over-express OTX2 protein, and a pharmaceutically acceptable carrier. Preferably, this pharmaceutical composition is formulated for intraocular injection.

For these aspects, the retinal degeneration is preferably related to RPE dysfunction. In particular, the retinal degeneration may be due to a disease selected from the group consisting of retinitis pigmentosa, age-related macular degeneration, retinal detachment, Leber congenital amaurosis, diabetic retinopathy, Best's disease, Stargardt's disease and choroideremia. Preferably, the retinal degeneration is due to retinitis pigmentosa.

BRIEF DESCRIPTION OF THE DRAWINGS

FIG. 12. Relative expression in cultured versus native RPE cells. Relative expression ($2^{-\Delta\Delta C_T}$) in cultured RPE cells was normalized by the expression in native RPE cells. GAPDH was used as housekeeping gene. Statistical analysis (GraphPad Prism, multiple t-test, Holm-Sidak method, with alpha=1.000%, n=3 biological triplicates).

FIG. 13. Relative expression in RPE cells transduced with AAV-Otx2, Otx2L versus control transduced RPE cells. Relative expression ($2^{-\Delta\Delta C_T}$) of genes in cultured RPE cells transduced with AAV-Otx2 and AAV-Otx2L was normalized by the expression in control cells (AAV-GFP transduced RPE). GAPDH was used as housekeeping gene. Statistic analysis (GraphPad Prism, Two-way ANOVA, Dunnett test, with alpha=1.000%, n=3 biological triplicates).

DETAILED DESCRIPTION OF THE INVENTION

Figure 1:
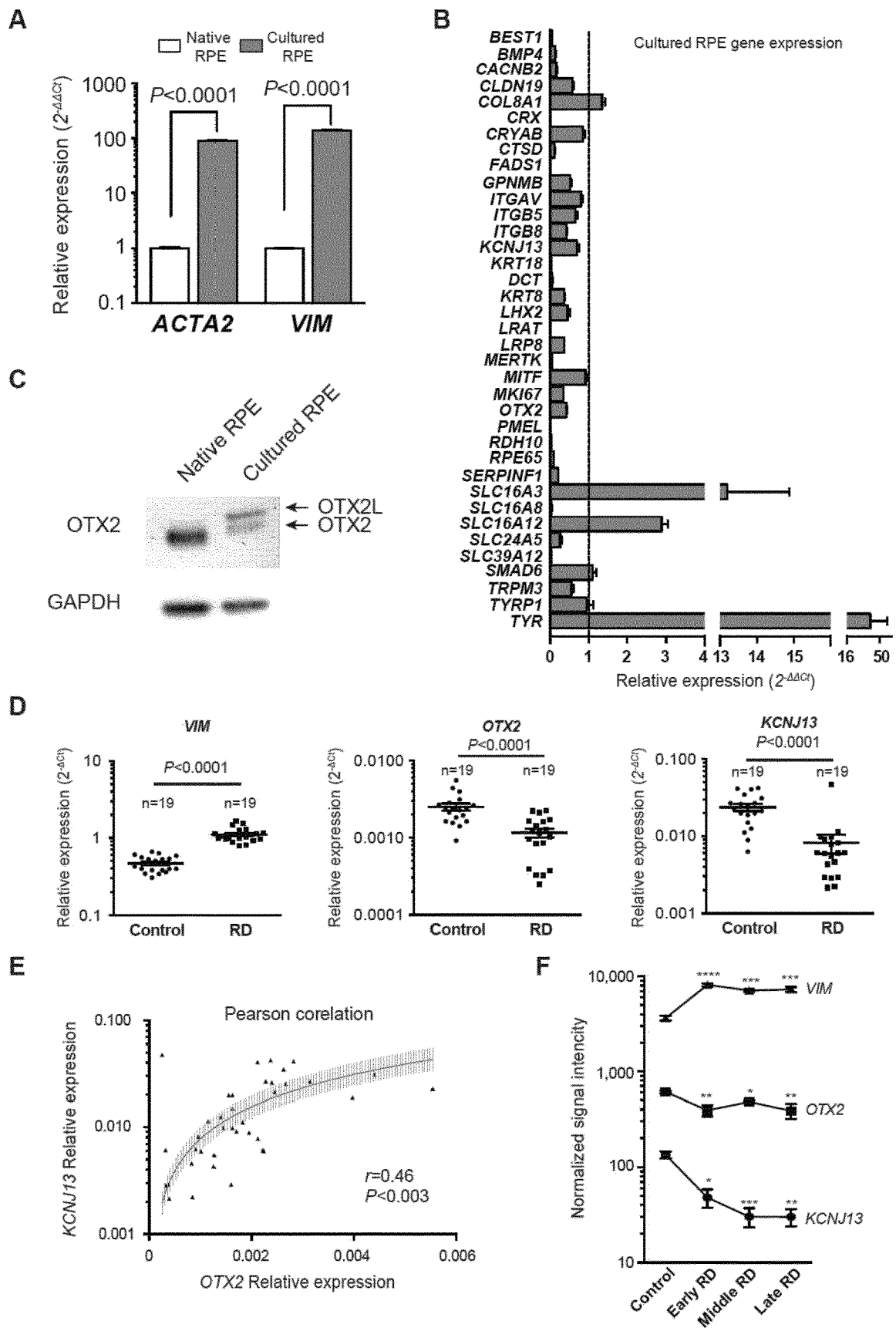
FIG. 1. Cultured retinal pigment epithelial cells undergo to epithelial-mesenchymal transition. (A) Expression of two mesenchymal markers, alpha smooth-muscle actin (ACTA2) and vimentin (VIM) by in cultured RPE cells measured by quantitative RT-PCR. (B) Differential expression measured by quantitative RT-PCR of 37 selected genes between in cultured and native RPE cells. Data are normalized to the housekeeping gene GAPDH and to their own expression level in native RPE cells. Means with standard deviation (SD) (n=3, ANOVA test). (C) Western blotting analysis of the expression of OTX2 in native and cultured RPE cells. (D) Expression of OTX2, KCNJ13 and VIM in patients after retinal detachment (RD) and post-mortem normal specimens. Individual data points were treated as means with standard error of the mean (SEM), analysis of variance (n=19, t-test, Welch correction). (E) Pearson correlation with r=0.46, P=0.003, and linear regression with P<0.0001. (F) Expression kinetics using Affymetrix data normalized using robust multi-array average (RMA) in RD and control specimens. Early RD: less than 1 week. Middle RD: between 1 week and 3 months. Late RD: superior to 3 months. (Dunnett ANOVA test).

The inventors herein demonstrated that over-expression of OTX2 by RPE cells improves the benefice of transplantation of these cells on photoreceptor survival. Indeed, using an in vivo model of retinitis pigmentosa, they showed that grafting of RPE cells infected with a recombinant adeno-associated viral vector encoding OTX2 dramatically increased the thickness of the outer nuclear layer (ONL) and improved photoreceptor response and survival in this model by comparison to grafting of non-overexpressing OTX2 RPE cells. Based on these results, it appears that grafting of OXT2 overexpressing RPE cells may be a valuable therapy for retinal degeneration diseases, in particular for diseases essentially caused by RPE layer dysfunction such as, for example, age-related macular degeneration, Leber congenital amaurosis or retinitis pigmentosa.

Accordingly, in a first aspect, the present invention relates to retinal pigment epithelial (RPE) cells engineered to increase the intracellular level of OTX2 protein for use in the treatment of retinal degeneration.

OTX2 protein, also known as orthodenticle homeobox 2 protein or homeobox protein OTX2, is a transcription factor. This protein plays a role in brain, craniofacial, and sensory organ development. During retina development, OTX2 regulates RPE specification, and photoreceptor and bipolar cell differentiation and maturation. OTX2 expression is maintained in these three cell types throughout life (Fossat et al., 2007).

The amino acid sequences of a number of different mammalian OTX2 proteins are known including, but being not limited to, human, pig, chimpanzee, dog, cow, mouse, rabbit or rat, and can be easily found in sequence databases.

Herein, the terms "peptide", "oligopeptide", "polypeptide" and "protein" are employed interchangeably and refer to a chain of amino acids linked by peptide bonds, regardless of the number of amino acids forming said chain.

OTX2 protein having an increased intracellular level in RPE cells according to the invention may be a native mammalian OTX2 protein, or a variant or functional fragment thereof.

As used herein, the term "native mammalian OTX2 protein" includes any naturally occurring alternative splice isoform or any naturally occurring allelic form of a mammalian OTX2 protein, in particular of human, pig, chimpanzee, dog, cat, cow, mouse, rabbit or rat OTX2 protein.

As used herein, the term "OTX2 protein variant" refers to a polypeptide sequence that is derived from a native OTX2 protein and comprises an alteration, i.e., a substitution, insertion, and/or deletion, at one or more (e.g., several) positions, but retains OTX2 activity. The variant may be obtained by various techniques well known in the art. In particular, examples of techniques for altering the DNA sequence encoding the native protein, include, but are not limited to, site-directed mutagenesis, random mutagenesis and synthetic oligonucleotide construction.

Preferably, as used herein, the tem' "variant" refers to a polypeptide having an amino acid sequence having at least 70, 75, 80, 85, 90, 95 or 99% sequence identity to the native sequence. As used herein, the term "sequence identity" or "identity" refers to the number (%) of matches (identical amino acid residues) in positions from an alignment of two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005). Alignment for purposes of determining percent amino acid sequence identity can be achieved in various ways that are within the skill in the art, for instance, using publicly available computer software available on internet web sites such as (see Worldwide Website: blast.ncbi.nlm.nih.gov/) or (see Worldwide Website: ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend =0.5, End gap penalty=false, End gap open=10 and End gap extend=0.5.

More preferably, the term "variant" refers to a polypeptide having an amino acid sequence that differs from a native sequence by less than 30, 25, 20, 15, 10 or 5 substitutions, insertions and/or deletions. In a preferred embodiment, the variant differs from the native sequence by one or more conservative substitutions, preferably by less than 15, 10 or 5 conservative substitutions. Examples of conservative substitutions are within the groups of basic amino acids (arginine, lysine and histidine), acidic amino acids (glutamic acid and aspartic acid), polar amino acids (glutamine and asparagine), hydrophobic amino acids (methionine, leucine, iso-leucine and valine), aromatic amino acids (phenylalanine, tryptophan and tyrosine), and small amino acids (glycine, alanine, serine and threonine).

As used herein, the term "functional fragment" refers to a fragment of a native OTX2 protein or of a variant as defined above, comprising at least 100, 150, 200 or 250 contiguous amino acids of said protein or variant, and exhibiting OTX2 activity. Preferably, the fragment comprises at least 100 contiguous amino acids of the N-terminus of OTX2 protein, i.e. the DNA binding domain involved in the transcriptional regulation activity.

OTX2 activity of a variant or fragment may be assessed by any method known by the skilled person. For example, OTX2 activity may be assessed using chromatin immuno-precipitation (ChIP) as detailed below in the experimental section and as described previously in Reichman et al., 2010, Dorval et al., 2006, and Pattenden et al., 2002. TYRP1 promoter has been reported to comprise OTX2 regulatory elements that bind OTX2 protein and thus promote its transcription factor activity (Martinez-Morales et al., 2003). Co-immunoprecipitation of TYRP1 promoter DNA and a variant or a fragment, thus indicates that this variant or fragment retains its capacity to bind to OTX2 regulatory elements and to promote transcription. OTX2 activity may be assessed using gene reporter assay as described in the article of Martinez-Morales et al., 2003.

In a particular embodiment, OTX2 protein having an increased intracellular level in RPE cells according to the invention is a human OTX2 protein or a variant or fragment thereof.

Human OTX2 protein is encoded by the gene OTX2 (Gene ID: 5015), also known as CPHD6 or MCOPS5. Alternative splicing results in multiple transcript variants encoding two distinct isoforms of OTX2 protein as identified by GenBank Accession numbers: NP_001257452.1 (isoform b, 289 amino acid length, SEQ ID NO: 15) and NP_001257454.1 (isoform a, 297 amino acid length, SEQ ID NO: 16).

OTX2 protein may comprise, or consist of, the amino acid sequence set forth in SEQ ID NO: 15, or SEQ ID NO: 16, or any variant or fragment thereof. Preferably, OTX2 protein comprises, or consists of, the amino acid sequence set forth in SEQ ID NO: 15, or SEQ ID NO: 16.

The retinal pigment epithelium (RPE) is the pigmented cell layer outside the neurosensory retina between the underlying choroid (i.e. the layer of blood vessels behind the retina) and overlying retinal visual cells (i.e. photoreceptors).

RPE cells are characterized by their cobblestone cellular morphology of black pigmented cells. They express several RPE markers including RPE65, the transcription factor MITF, the tight junction protein ZO-1 (TJP1), bestrophin (BEST1), MERTK, RDH10 and pigment epithelium derived factor (PEDF).

Preferably, RPE cells used in the present invention are mammalian RPE cells, more preferably human RPE cells.

In an embodiment, RPE cells are obtained from a donor (e.g. cadaver eye donor) or from the subject to be treated. Preferably, RPE cells are obtained from the subject to be treated. In this case, RPE cells are collected from the subject before to be engineered to increase the intracellular level of OTX2 protein and to be re-injected into the same subject (autologous transplantation).

In another embodiment, RPE cells are obtained from differentiation of stem cells, preferably human stem cells, into RPE cells. Examples of stem cells suitable to be differentiated into RPE cells include, but are not limited to, embryonic stem cells, induced pluripotent stem (iPS) cells, adult stem cells, hematopoietic cells, fetal stem cells, mesenchymal stem cells, postpartum stem cells, multipotent stem cells, or embryonic germ cells.

Preferably, stem cells are pluripotent stem cells, i.e. stem cells having the potential to differentiate into all cell types of a human or animal body, not including extra-embryonic tissues. These stem cells include both embryonic stem cells (ESCs) and induced pluripotent stem (iPS) cells.

Producing RPE cells from human embryonic stem cells may meet ethical challenges. According to one embodiment, embryonic stem cells are non-human embryonic stem cells. According to another embodiment, human embryonic stem cells may be used with the proviso that the method itself or any related acts do not include destruction of human embryos.

Induced pluripotent stem cells are stem cells artificially derived from a non-pluripotent cell, typically an adult somatic cell, by inducing a forced expression of specific genes (e.g. OCT4, SOX2, NANOG and LIN28 in human cells). One benefit of use of iPS cells is avoidance of the involvement embryonic cells altogether, and hence any ethical questions thereof.

Therefore, according to a preferred embodiment, RPE cells are iPS cell derived RPE cells. iPS cells may be obtained from the subject to be treated or from another subject. Preferably, iPS cells are derived from cells from the subject to be treated, in particular from fibroblasts of this subject.

RPE cells may be obtained from iPS cells using any differentiation method known by the skilled person. In particular, such RPE cells may be obtained from human iPS cells using the protocol described in Reichman et al., 2014. Briefly, fibroblasts cells are transfected with episomal vectors expressing OCT4, SOX2, NANOG, LIN28, c-MYC and KLF4 genes and RPE cells are obtained by differentiation of confluent iPS cells.

RPE cells may be produced from stem cells using any method known by the skilled person such as, for example, methods described in Reichman et al., 2014 or WO 2011/063005, depending on the type of stem cells used.

RPE cells used according to the invention are engineered to increase the intracellular level of OTX2 protein. The intracellular level of OTX2 protein is increased by comparison with the level in non-engineered RPE cells. These RPE cells are in vitro or ex vivo engineered before to be administered to the subject in need thereof.

As used herein, the term "engineered RPE cells" refers to RPE cells which are genetically or chemically modified to increase the intracellular level of OTX2 protein.

In an embodiment, the intracellular level of OTX2 protein is increased by direct introduction of this protein into the cells. The protein introduced into the cells may be any OTX2 protein as described above, in particular a native mammalian, preferably human, OTX2 protein, or a variant or functional fragment thereof.

Preferably, the intracellular level of OTX2 protein in engineered RPE cells is at least 1.5-fold higher, or 2, 3, 4, 5-fold higher, than the level in non-engineered RPE cells.

Like many homeoproteins, OTX2 is able to naturally transduce cells. However, optionally, in order to facilitate the entry of the OTX2 protein across the cell membrane and into the cell, the protein as defined above may be fused to a cell-penetrating peptide. Numerous cell-penetrating peptides are known in the art (see, e.g. Deshayes et al., Cell. Mol. Life Set, 2005, 62: 1839-1849; El-Andaloussi et al., Curr. Pharm. Design, 2005, 11: 3597-3611; Mae and Langel, Curr. Opin. Pharmacol. 2006, 6: 509-514) and can be used in the present invention.

Alternatively, OTX2 protein may be also introduced into RPE cells in combination with internalization carriers such as naturally entering proteins (e.g., protamin, histones, antibodies), viral components (e.g., Herpes VP22), protein transfection reagents (e.g., Chariot™, Pro-Ject™, Trans-Pass™ P, ProteoJuice™, PULSin™), cationic lipids, liposomes, nanoparticles (e.g., poly(lactic-co-glycolic acid)), dendrimers, polycations or small-molecule carriers (e.g., Okuyama et al. Nat Methods. 2007 February; 4(2): 153-9). OTX2 protein may also be directed injected into the cells.

In a preferred embodiment, RPE cells used according to the invention are genetically engineered to over-express OTX2 protein.

The expression level of OTX2 protein as defined above, may be determined by measuring the quantity of OTX2 protein produced in RPE cells, using any methods known by the skilled person. Usually, these methods comprise contacting a cell sample, preferably a cell lysate, with a binding partner capable of selectively interacting with the OTX2 protein present in the sample. The binding partner is generally a polyclonal or monoclonal antibodies, preferably monoclonal. Polyclonal and monoclonal antibodies anti-OTX2 are commercially available (e.g. anti-OTX2 antibody ab9566, Millipore). The quantity of the protein may be measured, for example, by semi-quantitative Western blots, enzyme-labeled and mediated immunoassays, such as ELISAs, biotin/avidin type assays, radioimmunoassay, immunoelectrophoresis or immunoprecipitation or by protein or antibody arrays. The reactions generally include revealing labels such as fluorescent, chemiluminescent, radioactive, enzymatic labels or dye molecules, or other methods for detecting the formation of a complex between the antigen and the antibody or antibodies reacted therewith.

The expression level of OTX2 may also be determined by measuring the quantity of OTX2 mRNA. Methods for determining the quantity of mRNA are well known in the art. For example the nucleic acid contained in the sample is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. An example of primer pair which may be used to quantify human OTX2 mRNA is constituted by the following primers: forward primer 5'-CTTCCTACTTTGGGGG-CATGGACTGTG-3' (SEQ ID NO.: 17) and reverse primer 5'-GCATTGGTACCCATGGGACTGAGTGTG-3' (SEQ ID NO.: 18). Other suitable primers may be easily designed by the skilled person.

As used herein, the term "overexpress" or "overexpression" refers to an expression level which is, after normalization, at least 1.5-fold higher, or 2, 3, 4, 5-fold higher, than the expression level in non genetically modified RPE cells. Expression levels may be normalized by using expression levels of proteins which are known to have stable expression such as RPLPO (acidic ribosomal phosphoprotein PO), TBP (TATA box binding protein), GAPDH (glyceraldehyde 3-phosphate dehydrogenase) or β-actin.

Overexpression of OTX2 protein in RPE cells may be obtained by any method known by the skilled person such as by increasing the transcription of the endogenous gene encoding OTX2, introducing an expression cassette or vector comprising a nucleic acid sequence encoding OTX2 protein, increasing the translation of an mRNA encoding OTX2, and/or decreasing the degradation of an mRNA encoding OTX2.

In an embodiment, RPE cells are genetically engineered to increase the transcription of the endogenous gene encoding OTX2. In particular, transcription of the gene encoding OTX2 may be increased by modifying or replacing its promoter. For example, the promoter of the gene may be replaced by a strong constitutive promoter such as the SV40 promoter, the CMV promoter, the dihydrofolate reductase promoter or the phosphoglycerol kinase promoter.

In another embodiment, RPE cells are genetically engineered by introducing an expression cassette or expression vector comprising a nucleic acid sequence encoding OTX2 into said cells.

The nucleic acid sequence may be any nucleic acid sequence encoding an OTX2 protein as described above, in particular a native mammalian, preferably human, OTX2 protein, or a variant or functional fragment thereof.

The coding sequences of a number of different mammalian OTX2 proteins are known including, but being not limited to, human, pig, chimpanzee, dog, cow, mouse, rabbit or rat, and can be easily found in sequence databases. Alternatively, the coding sequence may be easily determined by the skilled person based on the polypeptide sequence.

Preferably, the nucleic acid sequence is operably linked to one or more control sequences that direct the expression of said nucleic acid in RPE cells.

The control sequence may include a promoter that is recognized by the RPE cell. The promoter contains transcriptional control sequences that mediate the expression of OTX2 protein. The promoter may be any polynucleotide that shows transcriptional activity in RPE cells including mutant, truncated, and hybrid promoters. The promoter may be a constitutive or inducible promoter, preferably a constitutive promoter, and more preferably a strong constitutive promoter. The promoter may also be tissue-specific, in particular specific of RPE cells. Examples of suitable promoters include, but are not limited to, the SV40 promoter, the CMV promoter, the dihydrofolate reductase promoter, the phosphoglycerol kinase promoter, the RPE65 promoter, the tissue inhibitor of metalloproteinase 3 (Timp3) promoter and the tyrosinase promoter. Preferably, the promoter is the CMV promoter.

The control sequence may also include appropriate transcription initiation, termination, and enhancer sequences; efficient RNA processing signals such as splicing and polyadenylation signals; sequences that stabilize cytoplasmic mRNA; sequences that enhance translation efficiency (i.e., Kozak consensus sequence); and/or sequences that enhance protein stability. A great number of expression control sequences, e.g., native, constitutive, inducible and/or tissue-specific, are known in the art and may be utilized to drive expression of the nucleic acid sequence encoding OTX2.

Typically, the expression cassette comprises, or consists of, a nucleic acid sequence encoding OTX2 operably linked to a transcriptional promoter and a transcription terminator.

The nucleic acid sequence or expression cassette may be contained in an expression vector. The vector may be an autonomously replicating vector, i.e., a vector that exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one that, when introduced into the host cell, is integrated into the genome and replicated together with the chromosome(s) into which it has been integrated.

Examples of appropriate vectors include, but are not limited to, recombinant integrating or non-integrating viral vectors and vectors derived from recombinant bacteriophage DNA, plasmid DNA or cosmid DNA. Preferably, the vector is a recombinant integrating or non-integrating viral vector. Examples of recombinant viral vectors include, but not limited to, vectors derived from herpes virus, retroviruses, lentivirus, vaccinia viruses, adenoviruses, adeno-associated viruses or bovine papilloma virus.

Preferably, RPE cells are genetically engineered using a recombinant adenovirus, adeno-associated virus or lentivirus vector, i.e. by introducing into said cells a recombinant adenovirus, adeno-associated virus or lentivirus vector comprising a nucleic acid sequence encoding OTX2 protein operably linked to one or more control sequences. In a preferred embodiment, the vector is a recombinant adeno-associated virus vector, more preferably a vector derived from adeno-associated virus 2. Non-natural engineered variants and chimeric AAV may be used. In particular, the capsid proteins may be variants comprising one or more amino acid substitutions enhancing transduction efficiency. An AAV particle can comprise viral proteins and viral nucleic acids of the same serotype or a mixed serotype (i.e. pseudotyped AAV). For example, the recombinant AAV vector may be an AAV serotype 2/1 hybrid recombinant gene delivery system comprising AAV2 genome and AAV1 capsid proteins. Those skilled in the art are familiar with such vectors and methods for their construction and use, see e.g. WO 01/83692.

The nucleic acid construct, expression cassette or vector may be transferred into RPE cells using any known technique including, but being not limited to, calcium phosphate-DNA precipitation, DEAE-Dextran transfection, electroporation, microinjection, biolistic, lipofection, or viral infection.

The nucleic acid construct, expression cassette or vector described above may be maintained in the modified RPE cells in an ectopic form or may be integrated into the genome.

Engineered RPE cells as described above are used for the treatment of retinal degeneration.

In a preferred embodiment, the retinal degeneration is related to RPE dysfunction.

RPE cells constitute a major component of the blood-retinal barrier and loss of integrity of tight junctions and adherens junctions in RPE can disrupt photoreceptor homeostasis. RPE cells also phagocytosize tips of outer segments normally shed by photoreceptors, generate melanosomes to function as a light and heat sink, provide trophic factors, and recycle visual pigments.

As used herein, the term "RPE dysfunction" refers to disturbance of any of these functions and can thus induce photobleaching of melanosomes, accumulation of lipofuscin granules, impairment of outer segment phagocytosis, formation of drusen, and/or breakdown of the blood-retinal barrier. RPE dysfunction is known to be an underlining cause of various degenerative retinal diseases such as retinitis pigmentosa, age-related macular degeneration, retinal detachment, Leber congenital amaurosis, diabetic retinopathy, Best's disease, Stargardt's disease or choroideremia. RPE dysfunction may be due to a mutation in a RPE cell specific gene such as RPE65, MERKT, BEST1, CRB1, KCNJ13, LRAT, MAK, RP1L1, RGR, RDH12 or OTX2, or to an increase of RPE cell apoptosis. These mutations or the degree of apoptosis may be assessed by any method well known by the skilled person.

In an embodiment, the retinal degeneration is due to a disease selected from the group consisting of retinitis pigmentosa, age-related macular degeneration, retinal detachment, Leber congenital amaurosis, diabetic retinopathy, Best's disease, Stargardt's disease and choroideremia. Preferably, the retinal degeneration is due to retinitis pigmentosa.

In a further aspect, the present invention also provides a pharmaceutical composition comprising engineered RPE cells as described above.

The pharmaceutical composition is formulated in a pharmaceutically acceptable carrier according to the route of administration.

Preferably, the composition is formulated to be administered by intraocular injection, in particular to the subretinal space of the eye. Pharmaceutical compositions suitable for such administration may comprise the RPE cells, in combination with one or more pharmaceutically acceptable sterile isotonic aqueous or nonaqueous solutions (e.g., balanced salt solution (BSS)), dispersions, suspensions or emulsions, or sterile powders which may be reconstituted into sterile injectable solutions or dispersions just prior to use, which may contain antioxidants, buffers, bacteriostats, solutes or suspending or thickening agents.

Optionally, the composition comprising engineered RPE cells may be frozen for storage at any temperature appropriate for storage of the cells. For example, the cells may be frozen at about −20° C., −80° C. or any other appropriate temperature. Cryogenically frozen cells may be stored in appropriate containers and prepared for storage to reduce risk of cell damage and maximize the likelihood that the cells will survive thawing. Alternatively, the cells may also be maintained at room temperature of refrigerated, e.g. at about 4° C.

The amount of engineered RPE cells to be administered may be determined by standard procedure well known by those of ordinary skill in the art. Physiological data of the patient (e.g. age, size, and weight) and type and severity of the disease being treated have to be taken into account to determine the appropriate dosage.

The pharmaceutical composition of the invention may be administered as a single dose or in multiple doses. Each unit dosage may contain, for example, from 10,000 to 50,000 engineered RPE cells per µl.

The pharmaceutical composition may further comprise one or several additional active compounds such as corticosteroids, antibiotics, analgesics, immunosuppressants, trophic factors, or any combinations thereof.

All the embodiments of the RPE cells used according to the invention are also contemplated in this aspect.

In another aspect, the present invention also relates to a method for treating retinal degeneration in a subject in need thereof, comprising administering a therapeutically efficient amount of RPE cells engineered to increase the intracellular level of OTX2, preferably genetically engineered to overexpress OTX2, or a pharmaceutical composition of the invention.

As used herein, the term "subject" refers to an animal, preferably to a mammal including human, pig, chimpanzee, dog, cat, cow, mouse, rabbit or rat. More preferably, the subject is a human, including adult, child and human at the prenatal stage.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

In particular, the term "treatment of retinal degeneration" may refer to a preservation or an improvement of the light-detecting capacity of the photoreceptors, in particular with an increased rod response on electroretinogram recordings. This term may also refer to an increase of the thickness of the outer nuclear layer.

By a "therapeutically efficient amount" is intended an amount of engineered RPE cells administered to a subject that is sufficient to constitute a treatment as defined above of retinal degeneration.

In the method for treating retinal degeneration of the invention, the pharmaceutical composition or RPE cells are preferably administered intraocularly, more preferably by injection in the subretinal space of the eye.

The method of the invention may also further comprise administering at least one additional therapeutic agent to the subject. In particular, said therapeutic agent may be selected from the group consisting of a corticosteroid, an antibiotic, an analgesic, an immunosuppressant, or a trophic factor, or any combinations thereof.

All the embodiments of the RPE cells and the pharmaceutical composition of the invention are also contemplated in this aspect.

In another aspect, the present invention also relates to a method for preparing engineered RPE cells as described above for use in implantation into a patient in need thereof comprising providing RPE cells and modifying said cells to increase the level of OTX2 protein.

Preferably, RPE cells are obtained from differentiation of stem cells, more preferably from differentiation of induced pluripotent stem cells obtained from somatic cells, e.g. fibroblasts, of the subject to be treated.

Preferably, RPE cells are genetically engineered to overexpress OTX2 protein.

All the embodiments of the RPE cells, the pharmaceutical composition and the method for treating retinal degeneration of the invention are also contemplated in this method.

The inventors showed that RPE cells of the present invention are able to improve photoreceptor survival. Thus, in a further aspect, the present invention also relates to the use of engineered RPE cells as described above to improve in vitro or ex vivo retina cell survival. The present invention also relates to a method of in vitro or ex vivo culturing retina cells comprising culturing retina cells in the presence of engineered RPE cells as described above. The present invention also relates to a co-culture comprising retina cells and engineered RPE cells as described above.

All the embodiments disclosed for the engineered RPE cells are also contemplated in this aspect.

As used herein, the term "retina cells" refers to photoreceptors, amacrine cells, bipolar cells, horizontal cells and ganglion cells. In preferred embodiments, this term refers to photoreceptor cells.

In vitro or ex vivo culture of retina cells may be conducted using any method well known by the skilled person, e.g. as described in Léveillard et al., 2004.

Co-cultures of the invention may be used for any application. Examples of such applications include, but are not limited to, drug screening, toxicity assays, or production of cells for cellular therapy.

All patents, patent applications, provisional applications, and publications referred to or cited herein are incorporated by reference in their entirety, including all figures and tables, to the extent they are not inconsistent with the explicit teachings of this specification.

The following examples are given for purposes of illustration and not by way of limitation.

EXAMPLES

Materials and Methods

Animals

Pigmented dystrophic RCS (rdy−/−, p+) rats were maintained in the animal facility at Institute de la Vision, Paris. Adult (male and female) recipient animals were at age of PN18 the time of transplantation. All experiments have been conducted in accordance with the policies on the use of animals and humans in neuroscience research, revised and approved by the ethics committee in animal experiment Charles Darwin for the use of animals in ophthalmic and vision research. Animals were kept on a standard 12/12 hour light-dark cycle and all assessments of visual function were conducted in the first 8 h of the light phase. All animals were maintained on oral 210 mg/l cyclosporine A (Merck Millipore 239835) administered in the drinking water from day 2 prior transplantation until the day they were sacrificed.

RNA Purification

Post mortal human retina samples with or without retinal detachment, control samples, and pig primary retinal pigment epithelium cells native or cultured were placed in guanidine hydrochloride solution and total RNA was purified using cesium chloride ($CsCl_2$) method (Delyfer et al., 2013). Briefly, tissue/cell samples were homogenized in 6 M Guanidine HCl using polytron (Kimematica PT2100). After homogenization samples were incubated 10 min, in room temperature (RT) with 2 M potassium acetate pH 5.0 followed by 10 min centrifugation at 5,000 rpm at 20° C. The supernatant was mixed with 5.3 ml 100 mM of Tris-HCl pH 8, 1% N-laurylsarcosine, 3.2 g $CsCl_2$ and was transferred on top of 1.8 ml de CsCl/EDTA in polyallomer ultracentrifugation tubes (Rotor SW 41 TI, Beckman) to create a CsCl gradient. Samples were centrifuged using (Optima LE80k, Beckman) for 24 h at 35,000 rpm at 20° C. for 24 h. The pellet was resuspended in 150 µl of 10 mM Tris-HCl pH 7.5; 1 mM EDTA; 0.1% SDS et 150 µl de 10 mM Tris-HCl pH 7.5; 1 mM EDTA. Total RNA was purified using phenol-chloroform extraction and resuspended in diethylpyrocarbonate (DEPC) water. Denaturing gel electrophoresis assessed RNA integrity.

Reverse Transcription and Real-Time PCR

First stranded cDNA was synthesized from 1 µl g of total RNA using random primers (Promega) and Superscript II reverse transcriptase (Invitrogen) following manufacturer instructions. Briefly, 1 µg of total RNA after DNAse I (Life technologies, 18068-015) treatment and inactivation at 65° C. for 5 min, was mixed with 5 units (U) RNasin® Plus (Promega), 100 ng random primers (Promega), 10 mM dNTPs (Invitrogen), 0.1 M DTT and 4 U reverse transcriptase enzyme. Samples were incubated at 42° C. for 50 min and enzymatic reaction was inactivated by incubation in 72° C. for 15 min. The endogenous expression of genes in human samples, human induced pluripotent stem cell (iPS)-derived RPE cells and in primary pig RPE cells were quantified by real time RT-PCR in using gene specific primers. Primers efficiency was determined prior the analysis and only primers with efficiency ranking from 90%-110% and $R^2 \approx 1$ were used for the quantitative analysis. 10 ng cDNA was mixed with 0.1 mM forward-reverse primer mix and 1× power SYBR Green (Invitrogen, 4367659). Amplification and analysis of the amplitude (cycle threshold, Ct) was performed using (7500 real time PCR System, Applied Biosystems) and briefly the following sections, $1^{st}$, containing 1 cycle at 95° C.; $2^{nd}$, 40 cycles: 15 sec at 95° C. followed by 20 sec at 60° C.; $3^{rd}$ section, 1 cycle, 1 min at 95° C.; 30 sec at 55° C.; 30 sec á 95° C. The expression of each gene was normalized by the expression of housekeeping gene using the ΔCt formula following manufacturer instructions. For analysis in human retinal detachment and gene screening in hiPS-RPE and pig primary RPE cells, glyceraldehyde-3-phosphate dehydrogenase (GAPDH) was used As housekeeping gene For characterization of human iPS-RPE the 18S rRNA was used as housekeeping gene. For comparative analysis the results were calculated using the ΔΔCt formula following manufacturer instructions and fold expressed was presented as $2^{-\Delta Ct}$ and/or $2^{-\Delta\Delta Ct}$.

Plasmid Construction

The vector plasmid pAAV2-CMV-eGFP carried the adeno-associated virus 2 (AAV2) genome and the transgene cassette encoding eGFP under control of a cytomegalovirus (CMV) promoter. The plasmids pAAV2-CMV-Otx2v (splicing variants) were constructed by replacing the eGFP in pAAV2-CMV-eGFP plasmid by the CDS of Otx2 splicing variants into NotI (5') and BamHI (3') restriction enzymes sights. The rat Otx2 and Otx2L fragments were amplified from the plasmids LA0ACA144YK13CM1 and LA0AC-A6YL17.CONTIG respectively (see Worldwide Website: kbass.institut-vision.org/KBaSS/), via high fidelity PCR using the forward primer 5' GTGTCCAGGCG-GCCGCAAAAATGATGTCTTATCTAAA (SEQ ID NO: 1) and reverse primer 5' AATCGGATCCCGATATCT-CACAAAACCTGGAATTTCCA (SEQ ID NO: 2). The helper plasmid (pHelper) providing the three-adenoviral helper genes VA, E4 and E2A, as well the plasmid pLT-RC02, encoding for the proteins of AAV1 capsid (Acland et al., 2005).

Production of the AAV2.1 Viruses

The AAV2 vectors with transgene cassettes encoding for green fluorescent protein (GFP) or Otx2, and Otx2L splicing variants under control of the CMV promoter were packaged into an AAV1 capsid. Briefly, $15 \times 10^6$ HEK 293 cells were triple transfected with 12 µg pHelper plasmid, 10 µg pLT-RC02, and 6 µg of either pAAV2-CMV-eGFP, pAAV2-CMV-Otx2 or pAAV2-CMV-Otx2L plasmids. These constructs were mixed with 120 µl, 1 µg/µl polyethylenimine (PEI) and 500 µl of DMEM. At 48 h post transfection, cells were harvested. Supernatant was incubated for 2 h at 4° C. with 1× polyethylene glycol (PEG) solution (8% PEG, 5M NaCl). Cells were lysed by 3 cycles freezing/thawing resuspended in lysis buffer (0.15 M NaCl, 50 mM Tris-Cl pH 8.5). Cell lysate was combined with PEG pellet and viral particles were collected by iodixanol gradient (15%, 25%, 40% and 60%) and centrifuged as described (Dalkara et al., 2009). The 40% fraction containing the AAV viruses was collected and purified by 1×PBS, 0.001% pluronic. The viral particles were stored in PBS, 0.001% pluronic. Titers were determined by absolute quantification by real time PCR using the following primers 5' GGAACCCCTAGTGATGGAGTT (SEQ ID NO: 3) and 3' CGGCCTCAGTGAGCGA (SEQ ID NO: 4) that target the ITR sequence and expressed as viral genomes per µl (vg/µl).

Human Induced Pluripotent Stem Cell-Derived Retinal Pigment Epithelium Cells

The integration-free human iPS cell line, hiPSC-2 was generated from adult human dermal fibroblast from an 8 years old boy. Fibroblast cells were transfected with episomal vectors expressing OCT4, SOX2, NANOG, LIN28, c-MYC, and KLF4 and fully characterized by Reichman et al, (Reichman et al., 2014). HiPSC-2 were maintained onto mitomycin C inactivated mouse embryonic fibroblast feeder layer (Zenith Biotech) in ReproStem medium (ReproCELL) with 10 ng/ml of human recombinant basic fibroblast growth factor 2 (FGF2) (Preprotech). Cells were incubated at 37° C. in a standard 5% $CO_2$/95% air and mechanically passaged once a week. RPE cells were obtained by differentiation of confluent hiPSC-2 as described (Reichman et al., 2014). Patches of pigmented cells were mechanically dissected and expanded on gelatin-coated culture dishes, noted as passage 0, to reach confluence. RPE cells were characterized by the morphology, pigment expression and by immunocytochemistry detecting for RPE specific protein expression (MITF and ZO-1). Expression of RPE gene markers were determined using quantitative RT-PCR and specific primers. Human iPS cell-derived RPE cells can be propagated for up to four passages, retaining their RPE morphology (Singh et al., 2013). Gene expression studies were performed on cells at passage 1.

Pig Retinal Pigment Epithelium Primary Culture

Pig eyes were collected from three breeding: Pietrain, Large white and Landrace and were obtained from authorized slaughterhouse (Abattoir Guy Harang, Houdan, France). The eyes were disinfected with for 3 min in 95% ethanol and transferred in $CO_2$ independent medium (Invitrogen). A small incision was done using a needle at the ora serrata (3 mm of the cornea) and the eye was cut around cornea, which was removed afterwards. The eye globe was cleaned from lens vitreous and neural retina. RPE/choroid, eyecups were washed twice with PBS and filled with Trypsin-EDTA 0.25% up to two third of the eyecups and incubated at 37° C. for 1 h and 40 min. RPE cells were collected by gentle up and down pipetting and transferred into DMEM medium containing 20% FBS and 10 µg/ml gentamicin. RPE cells from 11 eyes were pooled together and plated into five 10 $cm^2$ dishes in the same medium. The culture medium was changed on day 1 and day 4. By days 5-6, the cultures became confluent and showed a cobblestone like appearance typical of RPE cells.

Chicken Cone-Photoreceptor Enriched Culture

Eyes from chicken embryos at stage 29 were dissected and cleaned in 1×PBS and transfer of the eyes in $CO_2$ independent medium. Using dissecting instruments, neural retina was isolated and carefully cleaned from cornea, vitreous, lens and any other remaining tissue. Transfer neural retina into fresh $CO_2$ independent medium and dissociated in small pieces with the help of dissecting tools. Transfer of the pieces into new tube. Trypsin-EDTA 0.25% dissociation at 37° C. for 20 min followed centrifugation. Trypsin reaction was stopped by adding medium M199 containing 10% FBS followed by centrifugation. Photoreceptor progenitors were incubated with CDM medium (50% M199 (Life Tec. 11150-059); 50% DMEM, supplements: 5 µg/ml insulin, 5 µg/ml sodium selenite; 16.1 µg/ml putrescine; 0.63 µg/ml progesterone; 100 µg/m prostaglandin; 375 µg/ml taurine; 2.56 µg/ml cytidine-5'-diphosphocho line; 1.28 µg/ml cytidine-5'-diphosphate ethanolamine; 0.2 µg/ml hydrocortisone; 0.02 µg/ml tri-iodotyrosine; 110 µg/ml Sodium pyruvate; 100 µg/ml linoleic acid.

In Vitro Transduction

For in vitro transduction, primary RPE cells and/or iPS-derived RPE cells were seeded in 12-well plates, $12 \times 10^6$ cells/well in DMEM containing 10% FBS. The following day, cells were washed with 1×PBS and incubated for 5 h with 300 µl of DMEM containing $6 \times 10^{10}$ viral particles (AAV2.1-GFP or AAV2.1-Otx2v splice variants). After 5 h incubation, the medium was adjusted to 10% FBS and 10 µg/ml gentamicin. The cells were incubated for 10 days at 37° C., 5% $CO_2$. The medium was changed once at day 5. For transplantation studies the primary RPE cells were incubated for 7 days with the virus used for transduction.

Western Blotting & Immunocytochemistry

Western blotting protocol is done as described in Léveillard et al., 2004. Briefly, transduced pig primary RPE cells were solubilized in lysis buffer [50 mM Tris-HCl-pH 7.5, 1 mM EDTA, 1 mM DTT, 50 mg/ml TLCK (Sigma), 1× protease inhibitors (Sigma), 10 µg/ml Triton X-100] followed by sonication. The antibodies used are the following: anti-OTX2 (R&D systems AF1979, 1/1,500), anti-ACTB (1/500). Immunolabeling of hiPS-RPE monolayer after 45 days incubation were done for ZO-1 and MITF. Briefly cells were fixed for 10 min in 4% formaldehyde and followed by 3 washes with 1×PBS. Blocking was performed for 1 h at room temperature with (PBS, 0.2% gelatin, and 0.25% Triton X-100) and followed by overnight incubation at 4° C. with the primary antibody. The antibodies used are the following: anti-ZO-1 (61-7300, Life technology 1/250) and anti-MITF (clone D5, M3621, DACO 1/200). Slides were washed three times in PBS with 0.1% tween-20 and then incubated for 1 h at room temperature with the appropriate secondary antibody conjugated with either Alex-aFluor 488 or 594 (Life Technologies, 1/600) and DAPI (1/1000). Fluorescent staining signals were captured with a DM6000 microscope (Leica microsystems) equipped with a CCD CoolSNAP-HQ camera (Roper Scientific) or using an Olympus FV1000 confocal microscope equipped with 405-, 488-, and 543-nm lasers. Confocal images were acquired using a 1.55- or 0.46-μm step size and corresponded to the projection of 4-8 optical sections.

Chromatin Immunoprecipitation

Chromatin Immunoprecipitation (ChIP) was performed as described previously (Reichman et al., 2010; Dorval et al., 2006; Pattenden et al., 2002). Briefly, fresh RPE cells were dissected from 6 pig eyes and pooled together. RPE was cross-linked with ice-cold 4% formaldehyde in PBS for 30 min, rinsed in PBS, and sonicated (Vibra Cell) in lysis buffer [1% SDS, 10 mM EDTA, 50 mM Tris-HCl pH 8.0] and protease inhibitors (Sigma) to an average DNA size of 800 bp. The sonicated sample was centrifuged at 15,000 rpm for 10 min at 4° C. and the supernatant was pre-cleared with G-sepharose beads (PI-20399, Ficher) for 1 h at room temperature (RT). Aliquots of 100 μl was diluted to 1.5 ml with dilution buffer (1% Triton X-100, 2 mM EDTA, 150 mM NaCl, 20 mM Tris-HCl pH 8.0) and subdivided in three reactions that were incubated for 1 h at RT with 1) no-antibody 2) 2.5 μg of anti-rabbit antibodies (111-035-045, Jackson lab) antibody 3) anti-OTX2 antibodies (ab9566, Millipore). Samples were centrifuged at 15,000 rpm for 10 min at 20° C. and the supernatant was mixed with 15 μl of protein G-sepharose beads, 150 μg ultrapure salmon sperm DNA (15632-011, Invitrogen) and 150 μg yeast tRNA (15401-011, Invitrogen) and incubated for 1 hour and 30 min at RT. Precipitates were washed sequentially for 10 min at RT with TSEI (0.1% SDS; 1% Triton X-100; 2 mM EDTA; 20 mM Tris-HCl pH 8.0; 150 mM NaCl), 4 times with TSEII (0.1% SDS; 1% Triton X-100; 2 mM EDTA; 20 mM Tris-HCl pH 8.0; 500 mM NaCl), once with buffer III (0.25 M LiCl pH 8.0; 1% nonidet P-40; 1% deoxycholate; 1 mM EDTA; 10 mM Tris-HCl pH 8.0), and finally three times with TE buffer (10 mM Tris-HCl pH 8.0; 1 mM EDTA pH 8.0). Samples were eluted and cross-links cleared by overnight incubation at 65° C. in 100 μl of elution buffer (1% SDS; 0.1 M NaHCO$_3$). DNA fragments were purified by phenol-chloroform extraction and resuspended in 70 μl of TE buffer. Semi quantitative PCR was used to amplify 2 μl of the immunoprecipated material. PCR reaction was performed in 25 μl for 94° C. 3 min, 40 cycles (94° C./15 sec/60° C. 15 sec/72° C. 30 sec), 72° C. 3 min. The primers used were designed to amplify fragments into the promoter genes: KCNJ13, forward 5'-GCAGGCCTTCCATGAT-TTTA (SEQ ID NO: 5) and reverse 5'-TGAGCTGTCA-GATGGCTTTG (SEQ ID NO: 6); SLC16A12, forward 5'-TGCCTGTCCCACTAGGAAGT (SEQ ID NO: 7) and reverse 5'-GCATCATTTGCCATGTGACT (SEQ ID NO: 8); RDH10, forward 5'-GGCAACAAGTCCCACCTAAA (SEQ ID NO: 9) and reverse 5'-GTTTACTTGGTGGGG-GAGGT (SEQ ID NO: 10); TYRP1, forward 5'-CCAAT-TTGCAGGGAACAAAT (SEQ ID NO: 11) and reverse 5'-TGCCTTAAATTGCCTTCTCAA (SEQ ID NO: 12); HGB, forward 5'-GAACGTCAGGATTCCCTTGA (SEQ ID NO: 13) and reverse 5'-CCATTGGGAGCTTCCTTGTA (SEQ ID NO: 14).

Retinal Pigment Cell Preparation and Transplantation

Figure 11:
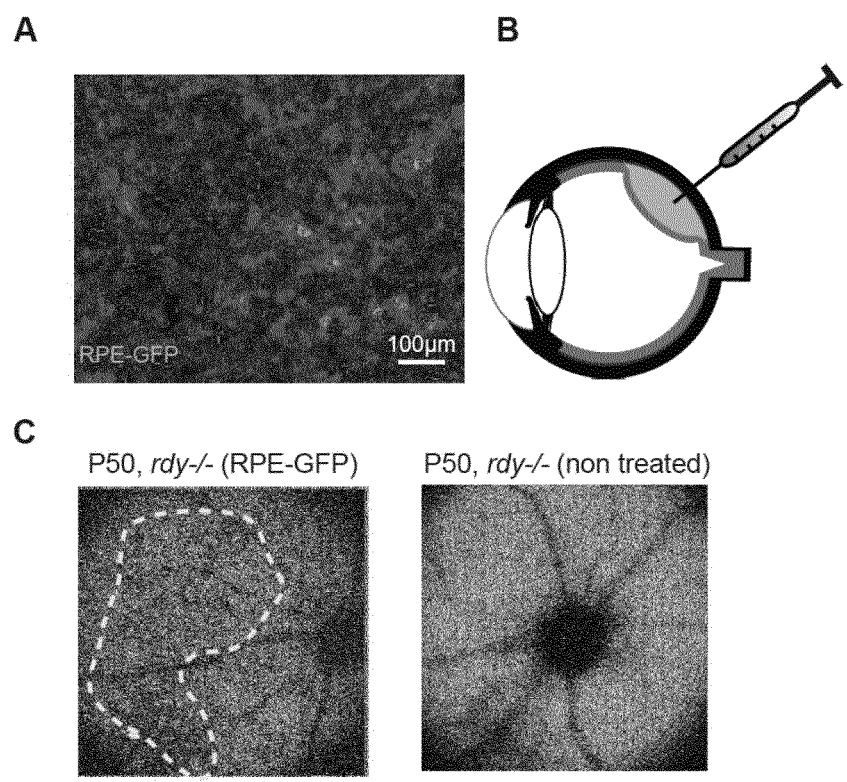
FIG. 11. Surgical procedure.

Transduced primary pig RPE cells with AAV2.1-GFP or AAV2.1-OTX2 incubated for 1 week as previously described prior transplantation. Cells were washed twice with HBSS (Hank's Balanced Salt Solution, Calcium, Magnesium, no phenol red) (Invitrogen) and dissociated with Trypsin-EDTA 0.05%. RPE cells were collected by gentle pipetting and transferred into HBSS containing 20% fetal bovine serum (FBS). The resulting pellet of cells were re-suspended at 25 000 cells/μl in HBSS. Surgery was performed under direct ophthalmoscopy through an operating microscope (FIG. 11). A blind protocol was employed which the sergeant was not informed about the identity (RPE-GFP or RPE-OTX2) cells were injected in each rat. Recipient rats were anaesthetized with a single intraperitoneal injection with a mixture of ketamine (1000 mg/kg) and xylazine (10 mg/kg) minimum 10 minutes before surgery. The blunt-ended 30 gauge Hamilton needle attached to a Hamilton syringe (10 μl, Model 1701 RN SYR, NDL Sold), was inserted tangentially through the sclera and RPE into the sub-retinal space. Cell suspensions were slowly injected 50 000 cells per eye. During all procedure eye dehydration was prevented by regular instillation of sodium chloride drops. After surgery both eyes, treated and non-treated were kipped closed for dehydration and destruction of the cornea. Rats were kept in chambers at 35° C. till recovery from anesthesia.

Optomotor Response

Contrast sensitivities and visual acuities of treated and untreated eyes were measured using optomotry Cerebral Mechanics Inc. Canada, and OptoMotry™, 1.77 system, by observing the optomotor responses of rats to rotating sinusoidal gratings (Alexander et al., 2007; Prusky et al., 2004; Pearson et al., 2012). Briefly, rats reflexively respond to rotating vertical gratings by moving their head in the direction of grating rotation. The protocol used yields independent measures of the acuities of right and left eyes based on the unequal sensitivities of the two eyes to pattern rotation: right and left eyes are most sensitive to counter-clockwise and clockwise rotations, respectively. A double-blind procedure was employed, in which the observer was "masked" to both the direction of pattern rotation, to which eye received the treatment and which eye received RPE-GFP or RPE-OTX2 cells. Briefly, each rat at PN50 was placed on a pedestal located in the center of four inward facing LCD computer monitors screens and was observed by an overhead infrared video camera with infrared light source. Once the rat became accustomed to the pedestal a 7 s trial was initiated by presenting the rat with a sinusoidal striped pattern that rotates either clockwise or counter-clockwise, as determined randomly by the OptoMotry™ software. Involuntary reflex head tracking responses are driven by the left (clockwise rotations) and right (counter-clockwise rotations) eyes, respectively. Contrast sensitivity was measured at a spatial frequency of 0.042 cycles/degree and at a speed of rotation of 0.5 hz. In order to assess visual acuity, gratings had a constant contrast of 100% and initial stimulus was a 0.042 cycles/degree. Using a staircase paradigm the program converges to measures of the acuities or contrast sensitivity of both eyes defined as the spatial frequency or % contrast yielding ≥70% correct observer responses. Acuity was defined as the highest spatial frequency yielding a threshold response. Similarly, contrast sensitivity was defined as 100 divided by the lowest percent contrast yielding a threshold response. While this protocol permits the separation of right and left eye sensitivities, the contralateral eye is not 'blind' to the stimulus.

Electroretinograms

ERGs were recorded at PN60 age of the rats or 42 days after transplantation, using an SEIM Biomedical system. For the transplantation experiments, test eyes received superior subretinal injections of 50 000 transduced RPE cells. A double masked protocol was employed such that the person performing the ERGs did not know which eye received transplantation and which eye remained untreated and which eye received RPE-GFP and RPE-OTX2. Following overnight dark adaptation, animals were prepared for recording under dim red light. Animals were anaesthetized with intraperitoneal injection of ketamine (100 mg/kg) and xylazine (10 mg/kg) and kept warm with a thermostatically controlled heat platform at 37° C. The pupils were dilated using 0.5% Mydriaticum, and the cornea was locally anesthetized with application of chlorohydrate of oxybuprocaine 1.6 mg/0.4 ml. Upper and lower lids were retracted to keep the eye open and proptosed. Viscotears liquid gel was placed on each cornea to keep it moistened after corneal contact golden electrodes. A stainless-steel reference electrode was inserted subcutaneously on the head of the rat and a second needle electrode inserted subcutaneously in the back of the rat served to ground the signal. Animals were left for a further 5 minutes in complete darkness prior to recording. Ganzfeld ERGs were obtained simultaneously from both eyes to provide an internal control. For scotopic recordings, single flash recordings were obtained at light intensities of 3 $\mu cds/m^2$, 30 $mcds/m^2$, 0.3, 3 and 10 $cds/m^2$ using a sampling frequency of 5 kHz, a flash duration of 4 ms, and a frequency stimulus of 0.5 Hz. Data were recorded from 50 ms before stimulus onset to 450 ms post-stimulus. Photopic cone ERGs were performed on a rod-suppressing background after 5-minute light adaptation, recordings were obtained at light intensities of 10 $cds/m^2$. The bandpass filter was set between 0 and 1 kHz. Each scotopic response represents the average of ten responses and each photopic ERG response represents the average of 5 responses from a set of five flashes of stimulation. The mean time to b wave peak for each group (n=7) was determined in each recording. Flickers cone ERGs respond were performed with flashlight at 10 Hz and with intensities of 0.3 $cds/m^2$.

Optical Coherence Tomography (OCT)

Treated rats at the age of PN60 were anesthetized and pupils were dilated as described above. Eye dehydration was prevented by regular instillation of sodium chloride drops. OCT images were recorded for both eyes using a spectral domain ophthalmic imaging system (Spectral domain Optical coherence tomography, OCT, Bioptigen 840 nm HHP; Bioptigen; North Carolina USA). The inventors performed rectangular scans consisting of a 2 mm by 2 mm perimeter with 1000 A-scans per B-scan with a total B-scan amount of 100. Scans were obtained first while centered on the optic nerve, and then with the nerve displaced either temporally/nasally or superiorly/inferiorly. OCT scans were exported from InVivoVue as AVI files. These files were loaded into ImageJ (version 1.47; National Institutes of Health, Bethesda, MD) where they were registered using the Stackreg plug-in. Scale of immage was performed converting the number of pixels to distance 3.11 pixels/μm. Outer nuclear layer (ONL) thickness was measured every 100 μm, ventral-dorsal and temporal-nassal, staring from the center (optic nerve) and cover the whole eye area given by OCT scan using a home made plugin for ImageJ. The mean of the thicknes of each point was calculated for group, non treated eye (n=6), RPE-GFP transplanted eyes (n=6) and RPE-OTX2 (n=7). ONL thickness was representated as 3D dencity maps.

In Vivo Scanning Laser Ophthalmoscope (SLO)

High-resolution infrared reflectance imaging and fluorescein angiography were performed with a modified scanning laser ophthalmoscope (SLO; Heidelberg Retina Angiograph, Heidelberg Engineering, Germany) using as previously described (Weismann et al., 1893).

Live Dead Assay

Live dead assay was performed as previously described (Léveillard et al., 2004). Briefly, transduced RPE cells with GFP, OTX2 (SEQ ID NO: 15) and OTX2L (SEQ ID NO: 16) were incubated for 1 week with CDM medium. Conditioned medium from RPE-transduced cells was collected and was added to primary retina cultures from chicken embryos (stage 29) prepared as described above and (Adler et al., 1989) in 96-well black tissue-culture plates (Corning) and incubated for 7 days at 37° C. and 5% $CO_2$. 14 negative control wells (conditioned medium) were also included. The inventors used a live/dead assay (Molecular Probes) to monitor cell viability. A masked protocol was employed such that the person performing the live dead analysis did not know which supernatant came from RPE-GFP or RPE-OTX2 transduced cells. For acquisition and cell counting, the inventors developed an algorithm based on the Metamorph software (Universal Imaging Corporation). They read plates under an inverted fluorescence microscope (TE 200, Nikon) equipped with a mercury epifluorescent lamp with two excitation filters (485 and 520 nm), two emission filters (520 and 635 nm), a 10× objective, a computer-driven motorized scanning stage (Märzhäuser) and a CCD camera. For the screening, they compared numbers of live cells with the mean number of live cells in the negative controls. Each assay was repeated three independent times with four replicates for each condition.

Hematoxylin and Eosin Embedding

Animals were anesthetized with ketamine and xylazine as previously and immediately perfused with 2.5% glutharaldehyde and 2% formaldehyde in phosphate buffered saline (PBS). Eyes were enucleated and incubated in fixative (2% formaldehyde) overnight. Lenses were removed and eyecups were washed 5 times in 5% sucrose. Eyecups were fixed for 1 h in 2% osmium tetroxide (Sigma Aldrich, 201030). This step was followed by dehydration with graded ethanol (50%, 70%, 95%) and 10 min incubation in propylene oxide. Afterwards eyes were incubated overnight at room temperature with mixture 1/1 (Araldite-epoxy resin/propylene oxide). Embedding was done with Araldite-epoxy resin mixture warmed at 65° C. over-night. Plastic sections of 1 μm thick were made along the sagittal axis using Leica EM UC6 ultra microtome and stained with toluidine blue (1% Borax, 1% toluidine blue).

Statistics

All data are expressed as means±standard error, unless otherwise stated. n=number of animals, eyes, or cells examined, as appropriate. Statistical significance was assessed using Graphpad Prism 6 software, and applying unpaired non parametric t-test, ANOVA with Bonferroni or Dunnett's correction for multiple comparisons, Welch correction, Kolmogorov-Smirnov, Wilcoxon matched-pairs, (2-tailed), where appropriate.

Results

Cultured Retinal Pigment Epithelial Cells Undergo an Epithelial-Mesenchymal Transition The inventors found that culturing primary pig RPE cells for one week induces the expression of two mesenchymal markers, alpha smooth-muscle actin (ACTA2) and vimentin (VIM) (FIG. 1A).

In order to elucidate the mechanism underlying this transition, the expression of a subset of 37 genes selected for being specifically expressed by RPE cells, presumably implicated in RPE function or photoreceptor survival, was measured. 27 of these genes (73%) were found to be down-regulated in cultured primary RPE cells, while three genes were up-regulated; SLC16A3, SLC16A12 and TYRP1 (FIGS. 1B and 12).

Among the down-regulated genes, the inventors noticed the presence of two transcription factors, CRX and OTX2. The expression of CRX was very severely reduced, while that of OTX2 was halved. Since it has been reported that OTX2 regulates the expression of CRX and that consequently CRX is downstream of OTX2, OTX2 expression was examined by western blotting. It was thus confirmed that OTX2 protein expression was reduced after one week in culture (FIG. 1C). The signal that corresponded to the OTX2 splice variant OTX2L was induced during this process. OTX2L encodes for an additional octapeptide GPWASCPA, 5 amino acids upstream of the homeodomain, but no additional function was never attributed to this variant.

An epithelial to mesenchymal transition also occurs in vivo, following retinal detachment, where it participates in its complication, proliferative vitreoretinopathy. The expression of VIM was examined in 19 human surgical specimens of retinal detachment as compared to 19 post-mortem specimens of neural retina by quantitative RT-PCR. An elevation of 2.37 fold of VIM expression correlated with retinal detachment (FIG. 1D). In the same specimens, OTX2 expression was reduced by 2.17 fold. Interestingly, one of its potent targets, the inwardly rectifying potassium channel KIR7.1, encoded by the KCNJ13 gene, was also down-regulated. Mutations in KCNJ13 cause snowflake vitreoretinal degeneration an autosomal dominant retinal disease, leading among other deficits to retinal detachment. A direct link between OTX2 and the expression of KCNJ13 was supported by the correlation (Pearson r-correlation, r=0.46, P<0.003 and linear regression with P<0.0001) of their expression within those specimens (FIG. 1E). When sorted according the delay between the occurrence of retinal detachment and the surgery, the expression of KCNJ13 was found to decrease between 1 week and three months (FIG. 1F).

Identification of Novel Otx2 Target Genes in Retinal Pigment Epithelium

In order to test if OTX2 regulates the expression of the 27 down-regulated genes, the inventors overexpressed rat OTX2, as well as independently OTX2L in pig primary RPE cells. OTX2 and OTX2L cDNAs were cloned into an adeno-associated viral vector and RPE cells were infected with AAV2.1-GFP, AAV2.1-OTX2 or AAV2.1-OTX2L. Seven days after transduction, the expression of OTX2 was verified by quantitative RT-PCR using primers that do not discriminate pig from rat OTX2 mRNA (FIG. 2A).

Figure 2:
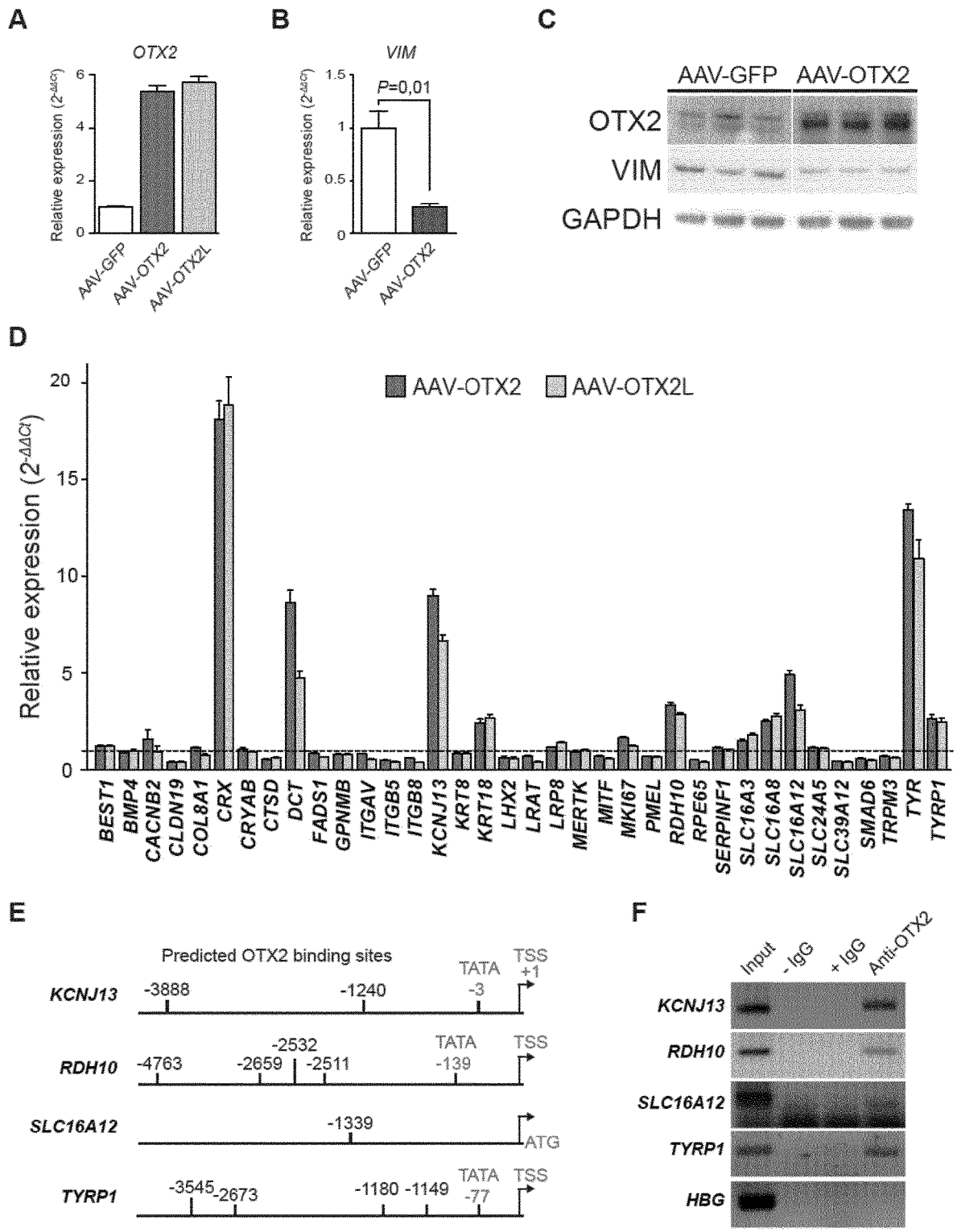
FIG. 2. Identification of novel OTX2 target genes in retinal pigment epithelium. (A) OTX2 gene expression analysis by quantitative RT-PCR in RPE cells infected with recombinant AAV vectors as indicated. (B) Expression of VIM in RPE cells infected with GFP and OTX2, n=4. (C) Western blot analysis of VIM in GFP and OTX2 transduced cultured RPE cells (n=3). (D) Relative quantitative RT-PCR in OTX2 and OTX2L transduced RPE cells. Data are normalized to the housekeeping gene GAPDH and to their own expression level in native RPE cells. Means with SD (n=3, ANOVA test). (E) Position of the predicted OTX2 binding elements in the analyzed promoters. (F) Chromatin immunoprecipitation in uninfected RPE cells. -IgG: no immunoglobulins. +IgG: non immune immunoglobulins.

It was noticed that ectopic expression of OTX2 reduced the expression of VIM by 4 fold (FIG. 2B). Western blotting analysis allowed the inventors to evaluate the level of OTX2 over-expression in that system since the antibody used do not distinguish the ectopic rat from endogenous pig OTX2 (FIG. 2C). This analysis shows that the expression of VIM protein is reduced by ectopic OTX2. Among the 37 selected genes, it was found that CRX expression was induced by almost 20 fold by both OTX2 and OTX2L confirming that OTX2 controls the expression of CRX in RPE cells (FIG. 2D). Similarly, the tyrosinase gene TYR was induced by 15 fold. The tyrosinase-related protein genes DCT and KCNJ13 were induced by OTX2 (~9 fold) and OTX2L (5 to 6 fold). Finally, the keratin gene KRT18, the retinol dehydrogenase gene RDH10, TYPR1 and the monocarboxylic acid transporter genes SLC16A8 and SLC16A12 were induced by 2 to 5 fold (FIG. 13). Interestingly, a risk allele within the SLC16A8 gene is at predisposing to age-related macular degeneration, a disease that involves dysfunction of the RPE (Fritsche et al., 2013).

To further establish the role of OTX2 in regulating the expression of these genes at the transcriptional level, chromosomal immunoprecipitation was performed on uninfected primary pig RPE cells. TYRP1 was used as a positive control since OTX2 has been reported to bind OTX2 regulatory elements within this promoter (Martinez-Morales et al., 2003). Candidate OTX2 regulatory elements were found in the KCNJ13, RDH10 and SLC16A12 promoters (FIG. 2E). Anti-OTX2 co-immunoprecipitated TYPR1 promoter DNA, while no signal was observed when immunoglobulins were omitted (−IgG) or when using non immune ones (+IgG) (FIG. 2F). Similar results were obtained with two genes, KCNJ13 and RDH10, whose expression is induced by OTX2. A third one, SLC16A12, showed also some degree of co-immunoprecipitation. The β-globin (HGB) promoter was used as negative control.

OTX2 Induces the Expression of KCNJ13, RDH10 and SLC16A8 in Human RPE Cells

Figure 9:
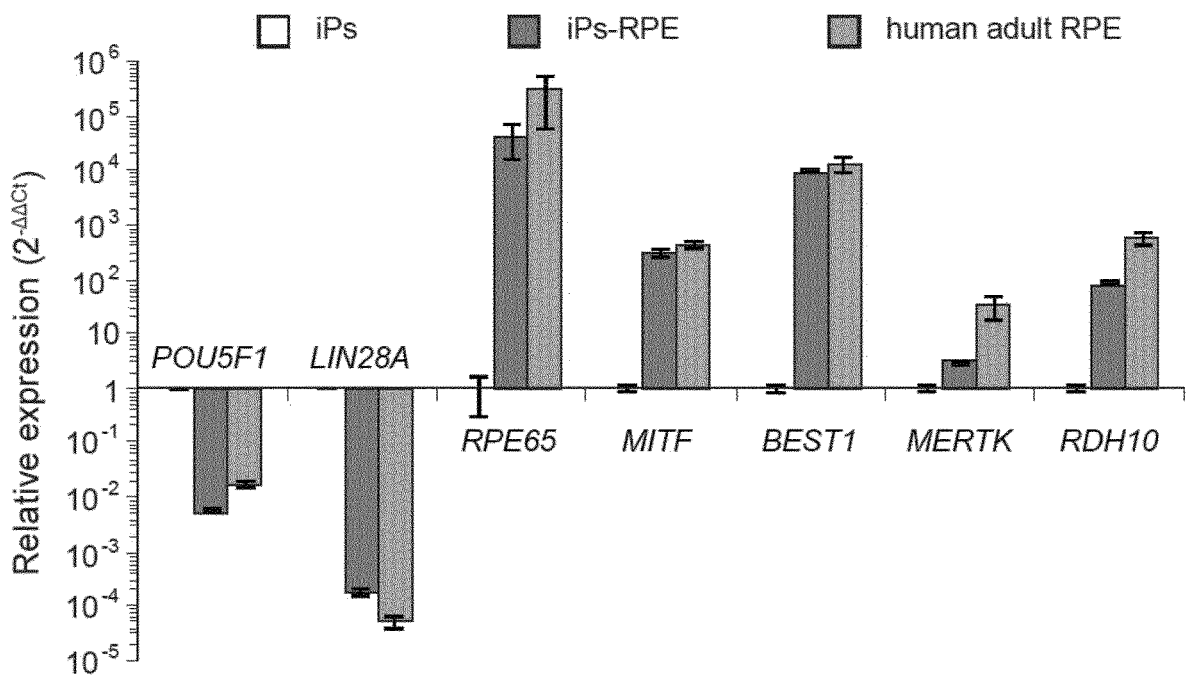
FIG. 9. Relative expression of RPE specific gene markers in non differentiated iPS, differentiated human iPs-derived RPE cells and human adult RPE cells. Data represented as means with SD.

To investigate whether these genes are targeted by OTX2 in human RPE cells, OTX2 was over-expressed in human induced pluripotent stem-derived RPE (iPS-RPE) (Reichman et al., 2014). These iPS-RPE cells express melanin, have typical cobblestone morphology, express the tight junction protein ZO-1 and the transcription factor MITF (Data not shown). The human iPS-RPE cells express several RPE markers as RPE65, MITF, BEST1 and MERTK, in addition to RDH10 to similar levels than RPE cells from a normal human post-mortem specimen, contrarily to the undifferentiated IPs cells (FIG. 9). This demonstrates that iPS cells have differentiated into RPE cells.

Figure 3A:
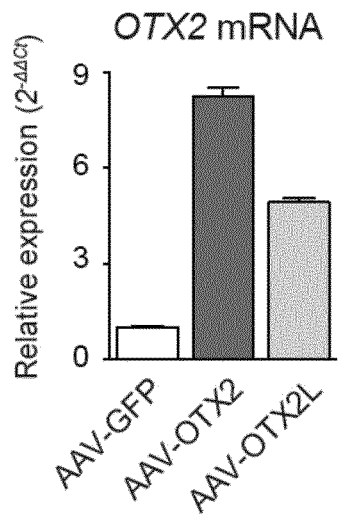
FIG. 3. OTX2 induces the expression of KCNJ3, RDH10 and SLC16A8 in human RPE cells. (A) Expression of OTX2 by quantitative RT-PCR in iPS-RPE cells infected with recombinant AAV vectors as indicated. Data are normalized to the housekeeping gene GAPDH and to their own expression level in native RPE cells. Means with SD (n=3, ANOVA test). (B) Expression of candidate genes by quantitative RT-PCR in iPS-RPE cells infected with recombinant AAV vectors as indicated. Data are normalized to the housekeeping gene GAPDH and to their own expression level in native RPE cells. Means with SD (n=3, ANOVA test).
Figure 3B:
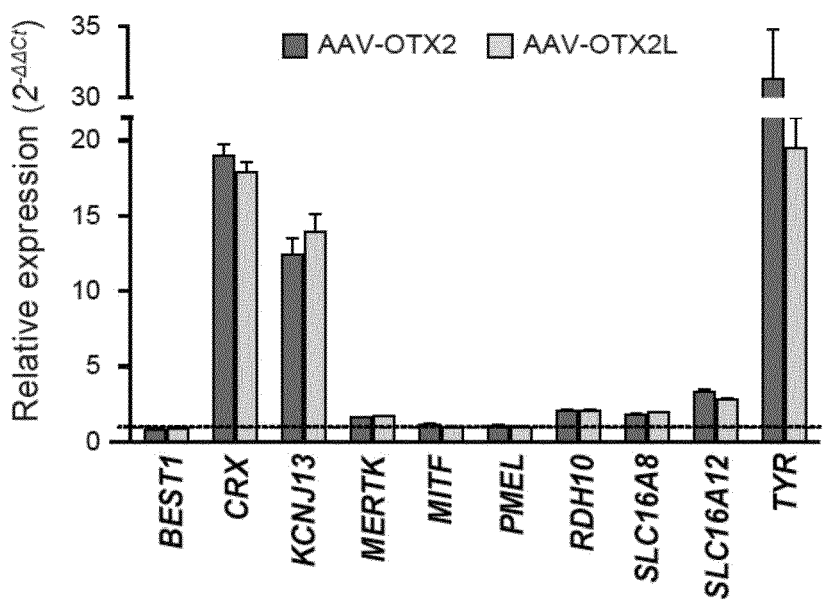

AAV infection resulted respectively in 8 and 5 fold increases in expression of Otx2 and Otx2L over endogenous OTX2 after seven days as shown by RT-PCR (FIG. 3C). The expression of the tyrosinase gene TYR was induced by 30 and 20 fold by OTX2 and OTX2L respectively, similarly to what was observed in the pig RPE cultures (FIG. 3D). CRX expression was increased by 18-fold. Four additional candidates OTX2 regulated genes were induced by ectopic expression of OTX2 and OTX2L; KCNJ13 (12.4 fold), SLC16A12, (3.3 fold), RDH10 (2.0 fold) and SLC16A8 (1.8 fold).

Figure 7:
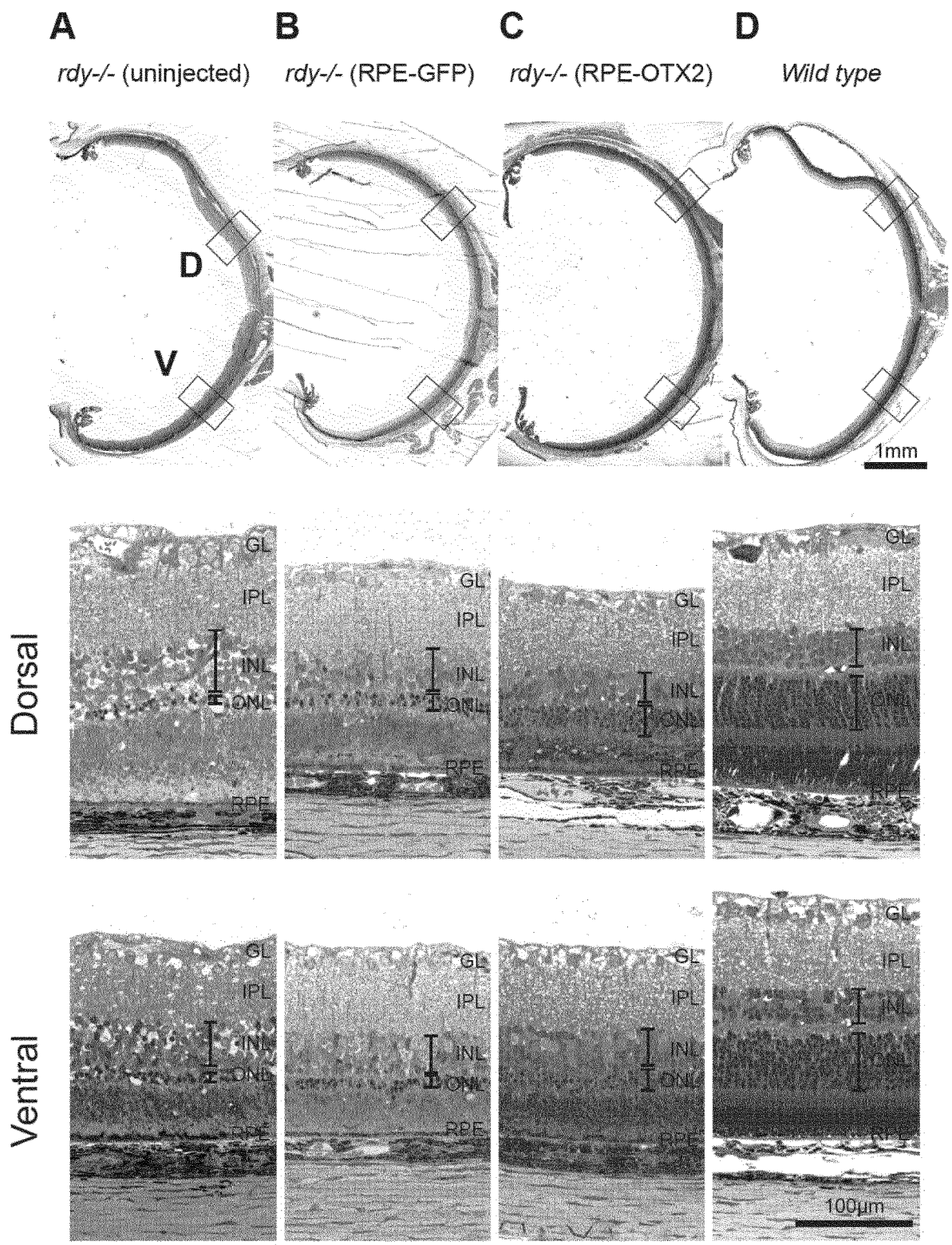
FIG. 7. Hematoxylin and eosin sections shows improvement in ONL thickness in transplanted eyes with RPE-OTX2 to be higher.

Grafting Genetically Modified RPE Cells Over-Expressing OTX2 in RCS Rat Improves Photoreceptor Function The effect of RPE transplantation was studied in the RCS rat, a recessive model of retinitis pigmentosa that carries a recessive mutation in the rdy gene encoding for MERTK protein. MERTK is a receptor tyrosine kinase expressed by RPE that is essential to the phagocytosis of the outer segments of photoreceptors. Consequently, MERTK mutations cause retinitis pigmentosa and rod photoreceptors of the RCS degenerate from post-natal (PN) 23 to PN60. The degeneration of rods is followed soon after by degeneration of the cones (D'Cruz et al. 2000; Pinilla et al. 2004; Girman et al. 2005). By PN60, rod and cone function were not recordable and histological examination showed that the outer nuclear layer (ONL), the layer of photoreceptor cells, was almost completely lost (FIG. 7A).

Using double blind procedure, the inventors injected into the subretinal space of the RCS rat eye at PN17, before degeneration starts, 50,000 RPE cells (n=7). Because it was not possible to prepare enough human iPS-RPE cells for this study, pig RPE cells were used. The injection was made in the dorsal part retina of right eyes while left eyes remained untreated. One week prior to transplantation, RPE cells were infected with a recombinant AAV2.1 vector encoding for GFP or OTX2. AAV2.1-GFP transduced RPE (RPE-GFP) cells were used as negative control. The presence of the transplanted cells was verified at PN60, after sectioning two eyes and using the fluorescence of GFP as reporter (data not shown).

Figure 4:
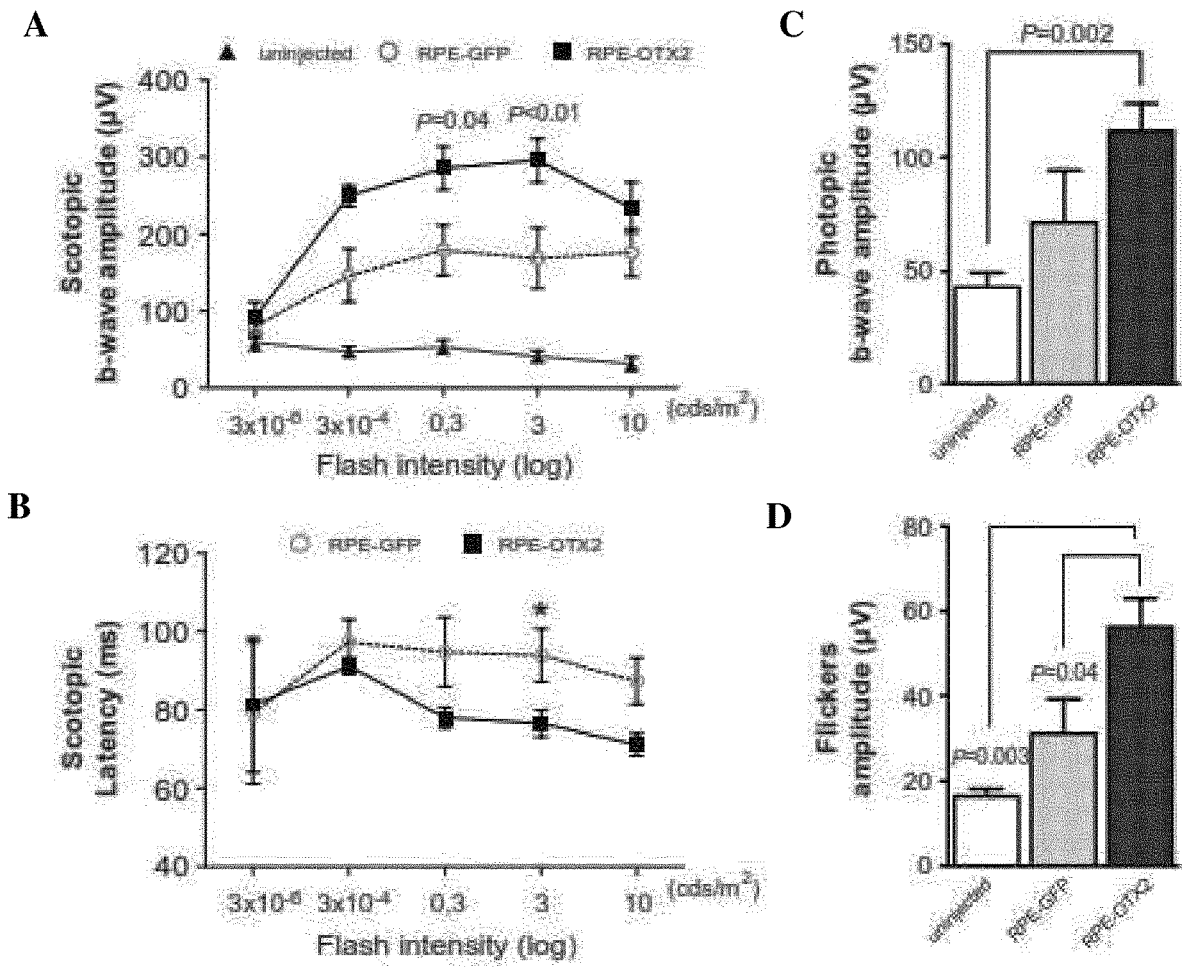
FIG. 4. Grafting of genetically modified RPE cells overexpressing OTX2 in RCS rat improves photoreceptor function. (A) Scotopic electroretinogram (ERG) comparison between non treated eyes and transplanted eyes with RPE-GFP and RPE-OTX2 grafts. (B) Comparison of the time latency to b-wave response in RPE-GFP and RPE-OTX2 grafted eyes. Individual points are shown as mean with SEM (n=7, Bonferroni ANOVA). (C) Photopic ERG for untreated (white bar) and RPE-GFP (light gray) and RPE-OTX2 (dark grey) grafted eyes. (D) Flickers ERG for untreated (white bar) and RPE-GFP (light gray) and RPE-OTX2 (dark grey) grafted eyes. Points are shown as mean with SEM, statistical test grafted-uninjected eyes (n=7, Wilcoxon matched-pairs), RPE-GFP and RPE-OTX2 (n=7, unpaired Kolmogorov-Smirnov test).
Figure 10:
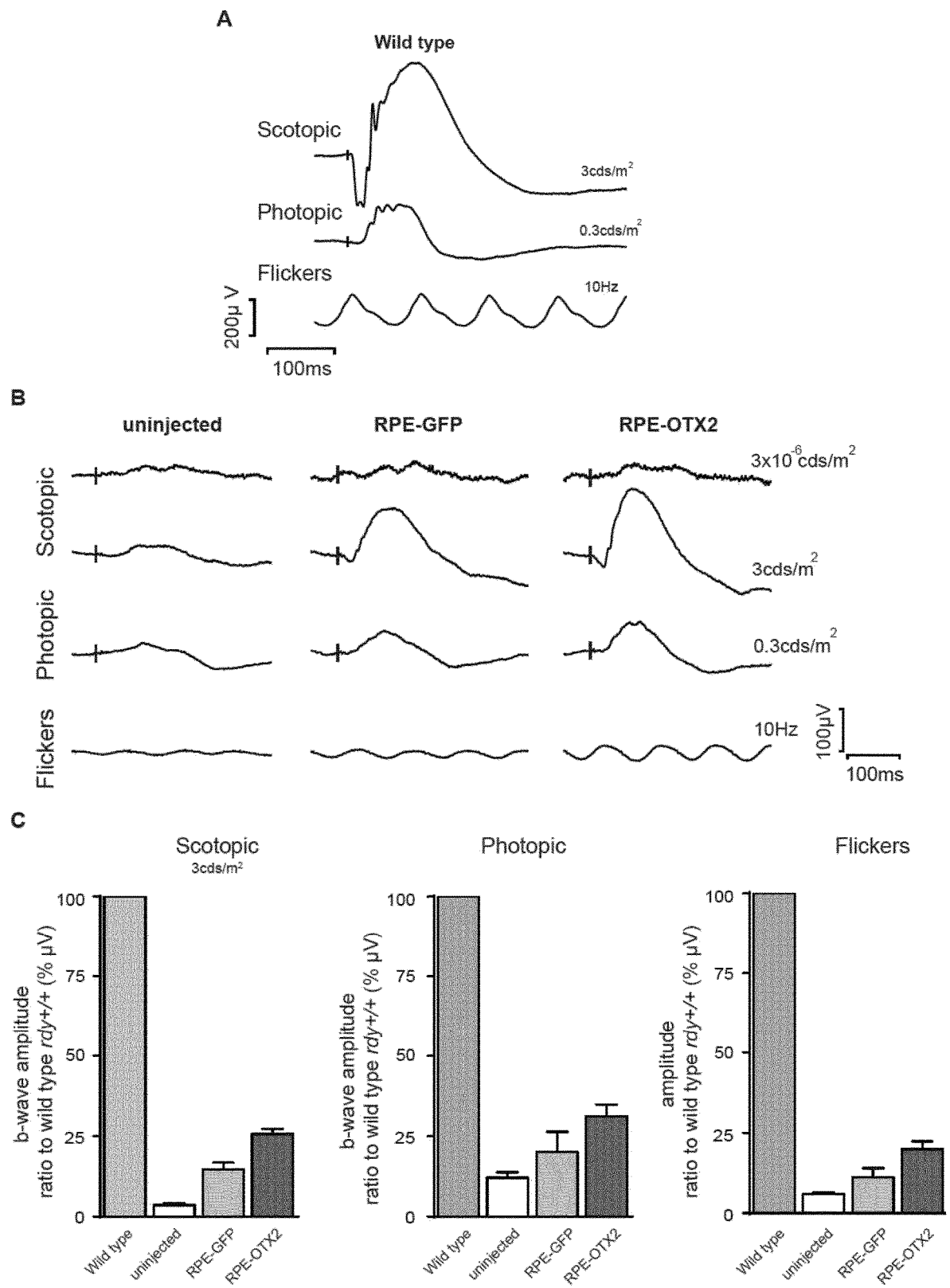
FIG. 10. ERG amplitude comparisons in the non injected and transplanted rdy−/− rats. (A) Characteristic ERG traces of wild type (rdy+/+) RCS rat. (B) Characteristic ERG amplitudes recorded at 42 post-injection days in uninjected dystrophic rat, RPE-GFP and RPE-OTX2 grafted animals. (C) ERG recording comparison between wild type, dystrophic uninjected, RPE-GFP and RPE-OTX2 grafted animals.

Electroretinograms (ERG) were reordered at PN60, 43 days after transplantation. The b-wave amplitude of the scotopic ERG (rod response) of the eyes treated by RPE-GFP or RPE-OTX2 cells was found to be significantly higher than for the contralateral non-injected eye from $3 \times 10^{-6}$ to 10 cds/cm$^2$ (FIGS. 4A and 10). The rod response from RPE-OTX2 transplanted eyes was higher than from RPE-GFP ones. The median of the response was almost 2 fold higher than that of GFP and correspond to 29.4% of that of the wild type, rdy+/+ rats. When considering latency, which means the time between the stimulus and the b-wave response, RPE-OTX2 grafted eyes responded faster to that of RPE-GFP eyes at high light intensities (FIG. 4B). The b-wave amplitude of the photopic ERG (cone response) was not significantly different between OTX2 and GFP, even if the response for RPE-OTX2 was higher, and both responses higher that of the untreated eyes (FIGS. 4C and 10). In such conditions, the signal arose from the response of both cone photoreceptors and bipolar cells. A pure cone response was recorded by flickers ERG. In those conditions, that the amplitude of the response was found to be higher in treated eyes and significantly higher for RPE-OTX2 than RPE-GFP (FIGS. 4D and 10).

Visual Behavior of the RCS Rats After Transplantation

Figure 5:
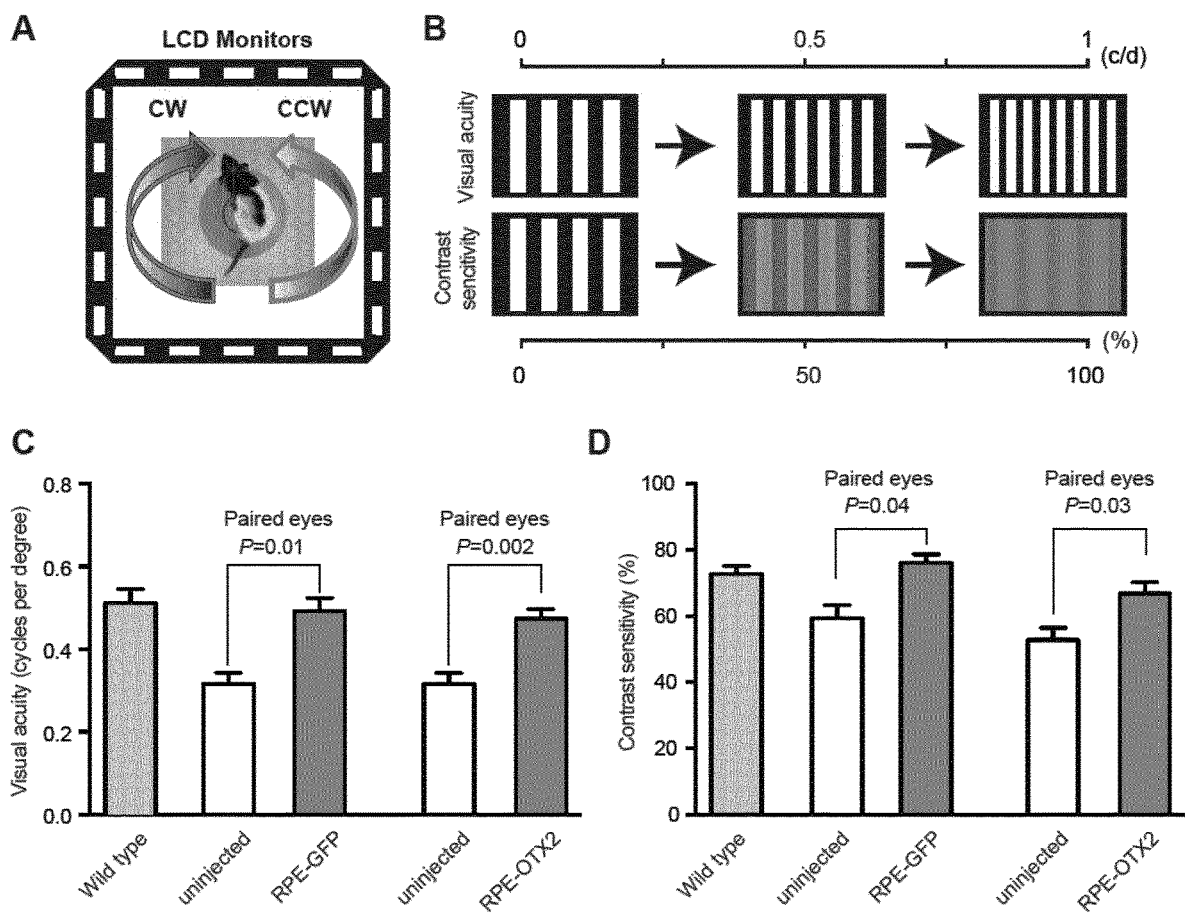
FIG. 5. Improvement in visual behavior of the RCS rats after transplantation. (A) Optokinetic chamber. (B) The Optomotory™ set-up. CW (Clockwise rotation: left eye drives response), CCW (Anticlockwise rotation: right eye drives response). (C) Visual acuity. (D) Contrast sensitivity. Points are shown as mean with SEM (n=7, Wilcoxon matched Paired t-test).

The visual behavior of treated rats was assessed using a double-blind protocol at PN50 by measuring optomotor head-tracking responses to rotating grating (FIG. 5A). Visual acuity and contrast sensitivity yield independent measures of the acuities of right and left eyes based on the unequal sensitivities of the two eyes to pattern rotation: right and left eyes are more sensitive to counter-clockwise and clockwise rotations, respectively. For visual acuity, the thickness of black and white stripes of fixed contrast is adjusted to the visual capacity of each animal, measuring visual acuity. For contrast sensitivity, it is the contrast of the dark/light grey stripes of equal thickness that is adjusted to measure contrast sensitivity (FIG. 5B).

Grafted eyes, RPE-GFP or RPE-OTX2, generated higher head tracking response with a mean visual-acuity response at 0.492 cycles per degree and 0.474 respectively compared to 0.335 contralateral, non injected eyes (FIG. 5C). Grafted eyes generated also an improvement of contrast sensitivity (FIG. 5D), 76% and 66.88% for RPE-GFP and RPE-OTX2 compared to 55.75% non-treated eyes.

Grafting RPE-OTX2 Cells Protects Rod Photoreceptors of the RCS Rats

Figure 6:
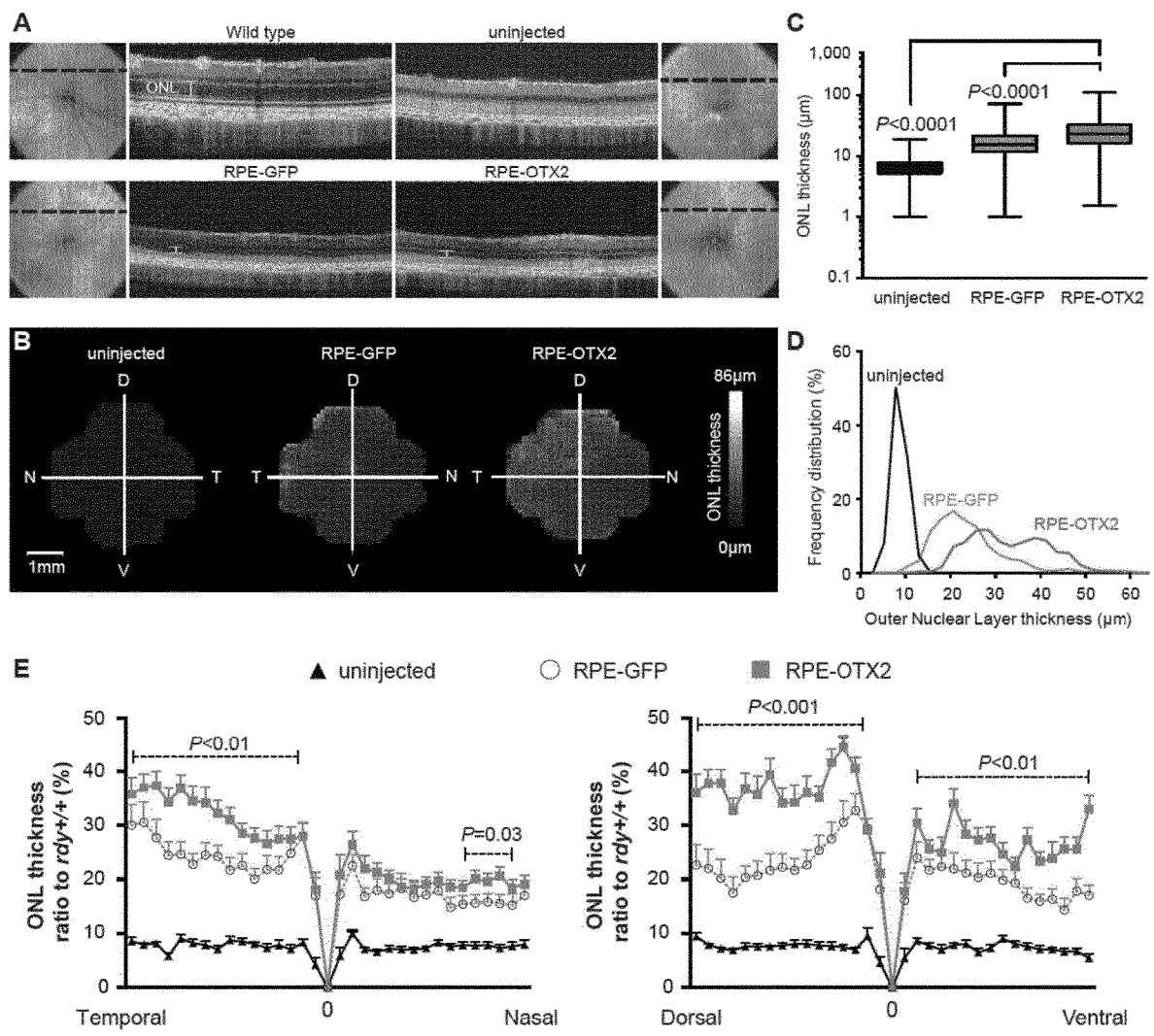
FIG. 6. Outer nuclear layer rescue in RPE-OTX2 treated eyes of dystrophic rats using optical coherence tomography (OCT). (A) OCT sections in wild type (rdy+/+), dystrophic untreated, RPE-GFP and RPE-OTX2 grafted eyes. (B) 3D representation of the mean outer nuclear layer (ONL) thickness in dystrophic uninjected, RPE-GFP and RPE-OTX2 grafted eyes. (C) ONL thickness comparisons between uninjected, RPE-GFP and RPE-OTX2 grafted eyes, mean with min and max (Mann Whitney test). (D) ONL thickness frequency distribution in uninjected, RPE-GFP and RPE-OTX2 grafted eyes. (E) Comparison of rational ONL thickness (% to wild type) temporal-dorsal and dorsal-ventral ONL thickness in middle sections of the eye. Measurements were presented as the average of each group of eyes with SEM. (Wilcoxon matched-pairs t-test). T: temporal, N: nasal, D: dorsal, V: ventral.

To investigate the protection of rods by transplantation, the thickness of the outer nuclear layer (ONL) that is composed of 95-97% rods in most rodents was measured at PN60. Measurements were made on the whole retina (9.5 mm$^2$) in optical sections spaced by 100 µm. The measures were taken every 100 µm on each section by optical coherence tomography (OCT) (on average 1,005 measurements per retina). On optical sections, the ONL is clearly identified by comparing the wild type retina to that of the uninjected RCS rat where this layer is absent (FIG. 6A). A three-dimensional map of the retina was reconstructed using the mean ONL thickness at each position over the entire retinal surface. The ONL was overall thicker in the transplanted eyes as seen by the predominance of the white color over the surface of the image (FIG. 6B). The map shows a gradual increase in ONL thickness toward the dorsal-temporal quarter, where the cells were injected. The ONL over the whole retina was thicker in RPE-OTX2 compared to RPE-GFP eyes (FIG. 6C). On 95% of the retinal surface, the ONL was 6.69 µm thick on average for the uninjected eyes, while it was 17.59 and 25.39 µm for RPE-GFP and RPE-OTX2 respectively. The ONL thicknesses were distributed between 6-32 µm for RPE-GFP eyes and shifted to 13-42 µm in RPE-OTX2 eyes (FIG. 6D). The bimodal aspect of both curves results from the protection of rods at the injection site and not from the presence of the transplanted cells themselves in the measurement. Data were normalized over the two central sections, temporal to nasal (TN) and dorsal to ventral (DV) with the ONL thickness of the wild type (rdy+/+) eyes (FIG. 6E). The inventors found that ONL was twice thicker in RPE-OTX2 than RPE-GFP grafted eyes at the injection site, the dorso-temporal quadrant of the retina. This corresponds to ~40% of the thickness of the ONL in wild type eyes, ~20% for GFP and ~10% for untreated RCS eyes. The thickness of the ONL of the transplanted RCS eyes was also thicker in the opposite part of the retina, the nasal-ventral quadrant.

The animals were sacrificed at PN75 and the eyes were sectioned. Hematoxylin and eosin staining showed disorganization of the inner retinal layer in addition to the thinning of the ONL in the untreated RCS eyes (FIG. 7A). Interestingly the transplantation of RPE cells genetically modified with OTX2 prevented this secondary event to a larger extend than RPE-GFP cells (FIGS. 7B and C). The organization of the inner retinal layer resembled that of the wild type (rdy+/+) eyes (FIG. 7D).

Figure 8:
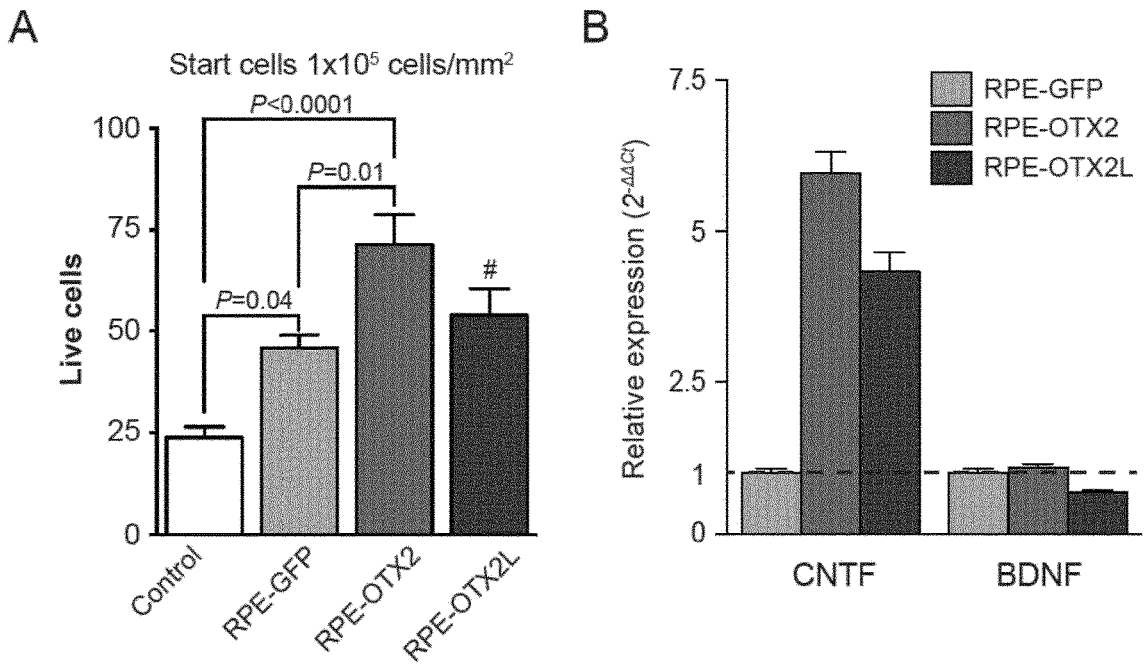
FIG. 8. Viability activity of RPE-GFP and RPE-OTX2 cells. (A) Survival activity of supernatant from GFP and OTX2 transduced pig primary RPE cells. Control represent conditioned non-cell incubated medium. The results represent the sum of four independent experiments. #: Significant only to control. Points presented as mean with SEM (n=6, Holm-Sidac multiple comparison ANOVA). (B) Expression of CNTF and BDNF in RPE cells infected with recombinant AAV vectors as indicated. GAPDH was used as housekeeping gene. Data are normalized by the level of expression in control AAV-GFP transduced cells. Means with SD; (n=3, ANOVA test).

RPE-OTX2 Modified Cells Secrete Neurotrophic Factors Protecting Cone Photoreceptors Photoreceptor rescue at distance from the injection site with RPE-GFP and RPE-OTX2 was indicative of a paracrine effect originating from the grafted RPE cells. The inventors used cone-enriched primary cultures from chicken embryos to investigate the presence of neurotrophic factors in the conditioned medium of transduced RPE cells (Léveillard et al. 2004). Conditioned media harvested from pig primary RPE cells infected with the AAV vectors were added to chicken retinal cultures. After 7 days of culture, the viability of the cells was scored using live/dead assay (Leveillard et al. 2004). RPE cells naturally secreted protective molecules. Nevertheless, as compared to RPE-GFP, RPE-OTX2 induced cell survival to a larger extent (FIG. 8A). The conditioned medium from OTX2 transduced pig RPE cells promoted increases cell survival 3 fold more than the negative control (medium alone) and 2 fold when compared to medium from GFP transduced RPE cells. Quantitative RT-PCR analysis of RNA isolated from RPE cells transduced with OTX2 showed that the expression of ciliary neurotrophic factor (CNTF) was induced by OTX2 while that of brain-derived neurotrophic factor (BDNF) remained unchanged (FIG. 8B).

REFERENCES

Acland et al. Mol Ther. 2005 December; 12(6):1072-82
Adler et al. 1989. Science (New York, N.Y.) 243:391-393
Alexander et al. 2007. Nature medicine 13:685-687.
Bennett et al. 2012. Sci Transl Med 4:120ra115.
Birch et al. 2013. Am J Ophthalmol 156:283-292 e281.
Byrne et al. 2015. J Clin Invest.
Da Cruz et al. 2007. Prog Retin Eye Res 26:598-635.
Dalkara et al. 2009. Mol Ther 17:2096-2102.
D'Cruz et al. 2000. Human molecular genetics 9:645-651.

Delyfer et al. 2013. Journal of visualized experiments: JoVE.
Dorval et al. 2006. J Biol Chem 281:744-751.
Fossat et al. 2006. EMBO Rep 7:824-830
Fritsche et al. 2013. Nat Genet 45:433-439, 439e431-432.
Girman et al. 2005. Vision Res 45:343-354.
Gouras et al. 1989. Prog Clin Biol Res 314:659-671.
LaVail et al. 1998. Invest Ophthalmol Vis Sci 39:592-602.
Léveillard et al. 2004. Nature genetics 36:755-759.
Léveillard et al. 2007. Med Sci (Paris) 23:240-242.
Litchfield et al. 1997. Exp Eye Res 64:655-666.
MacLaren et al. 2006. Nature 444:203-207.
Martinez-Morales et al. 2003. J Biol Chem 278:21721-21731
Pattenden et al. 2002. EMBO J 21:1978-1986.
Pearson et al. 2012. Nature 485:99-103.
Pinilla et al. 2004. Vision Res 44:2467-2474.
Prusky et al. 2004. Investigative ophthalmology & visual science 45:4611-4616.
Reichman et al. 2010. Hum Mol Genet 19:250-261.
Singh et al. 2013. Invest Ophthalmol Vis Sci 54:6767-6778
Weismann, A., and Spencer, H. 1893. Die Allmacht der Naturzüchtung, eine Erwiderung an Herbert Spencer. Jena: Fischer. 96 p. pp.
Weismann, A., Parker, W. N., and Rönnfeldt, H. 1893. The germ-plasm: a theory of heredity. London: W. Scott. xxiii, 477 p. pp.
Yang et al. 2009. Mol Ther 17:787-795.

The invention claimed is:

1. A method of treating retinitis pigmentosa in a mammal having retinitis pigmentosa, said method comprising the intraocular administration, by injection into the subretinal space of the eye of said mammal, of mammalian primary retinal pigment epithelial (RPE) cells or induced pluripotent stem cell-derived RPE cells overexpressing mammalian orthodenticle homeobox 2 protein (OTX2 protein), thereby increasing intracellular levels of OTX2 protein in the mammal, wherein the RPE cells overexpress OTX2 protein and comprise an AAV2 viral vector comprising a nucleic acid sequence encoding an OTX2 protein comprising SEQ ID NO: 15 or SEQ ID NO: 16.

2. The method according to claim 1, wherein said OTX2 protein consists of SEQ ID NO: 15.

3. The method according to claim 1, wherein said OTX2 protein consists of SEQ ID NO: 16.

4. The method according to claim 1, wherein the nucleic acid sequence encoding said OTX2 protein is operably linked to one or more control sequences.

5. The method according to claim 1, wherein the expression levels of OTX2 protein in said RPE cells overexpressing OTX2 are, after normalization, at least 1.5-fold higher than levels of OTX2 in RPE cells that do not comprise a viral vector for expressing OTX2 protein, said OTX2 protein comprising SEQ ID NO: 15 or SEQ ID NO: 16.

6. The method according to claim 1, wherein the RPE cells are administered in the form of a pharmaceutical composition comprising a pharmaceutically acceptable carrier.

7. The method according to claim 6, wherein said composition is formulated for subretinal injection.

8. The method according to claim 1, wherein the RPE cells are obtained from a mammalian donor or from the mammal to be treated.

9. A method of treating age-related macular degeneration (ARMD) in a mammal having ARMD said method comprising the intraocular administration, by injection into the subretinal space of the eye of said mammal, of mammalian primary retinal pigment epithelial (RPE) cells or induced pluripotent stem cell-derived RPE cells overexpressing mammalian orthodenticle homeobox 2 protein (OTX2 protein), thereby increasing intracellular levels of OTX2 protein in the mammal, wherein the RPE cells overexpress OTX2 protein and comprise an AAV2 viral vector comprising a nucleic acid sequence encoding an OTX2 protein comprising SEQ ID NO: 15 or SEQ ID NO: 16.

10. The method according to claim 9, wherein said OTX2 protein consists of SEQ ID NO: 15.

11. The method according to claim 9, wherein said OTX2 protein consists of SEQ ID NO: 16.

12. The method according to claim 9, wherein the nucleic acid sequence encoding said OTX2 protein is operably linked to one or more control sequences.

13. The method according to claim 9, wherein the expression levels of OTX2 protein in said RPE cells overexpressing OTX2 are, after normalization, at least 1.5-fold higher than levels of OTX2 in RPE cells that do not comprise a viral vector for expressing OTX2 protein, said OTX2 protein comprising SEQ ID NO: 15 or SEQ ID NO: 16.

14. The method according to claim 9, wherein the RPE cells are administered in the form of a pharmaceutical composition comprising a pharmaceutically acceptable carrier.

15. The method according to claim 14, wherein said composition is formulated for subretinal injection.

16. The method according to claim 9, wherein the RPE cells are obtained from a mammalian donor or from the mammal to be treated.

17. The method according to claim 1, wherein said retinitis pigmentosa results from degeneration or dysfunction of retinal pigmented epithelium.

18. The method according to claim 9, wherein said ARMD results from degeneration or dysfunction of retinal pigmented epithelium.

* * * * *